US009724531B2

(12) United States Patent
Schmidt

(10) Patent No.: US 9,724,531 B2
(45) Date of Patent: Aug. 8, 2017

(54) DOUBLE HELIX CONDUCTOR WITH LIGHT EMITTING FLUIDS FOR PRODUCING PHOTOBIOMODULATION EFFECTS IN LIVING ORGANISMS

(71) Applicant: Medical Energetics Ltd., Galway (IE)

(72) Inventor: David G. Schmidt, Poway, CA (US)

(73) Assignee: Medical Energetics Ltd., Galway (IE)

( * ) Notice: Subject to any disclaimer, the term of this patent is extended or adjusted under 35 U.S.C. 154(b) by 402 days.

(21) Appl. No.: 14/506,462

(22) Filed: Oct. 3, 2014

(65) Prior Publication Data
US 2015/0119631 A1 Apr. 30, 2015

Related U.S. Application Data

(60) Provisional application No. 61/962,012, filed on Oct. 28, 2013.

(51) Int. Cl.
A61N 2/00 (2006.01)
A61N 2/02 (2006.01)
A61N 5/06 (2006.01)
A61N 1/40 (2006.01)
H01F 5/00 (2006.01)

(52) U.S. Cl.
CPC .............. *A61N 2/002* (2013.01); *A61N 1/40* (2013.01); *A61N 2/02* (2013.01); *A61N 5/06* (2013.01); *H01F 5/00* (2013.01)

(58) Field of Classification Search
CPC ........ A61N 2/02; A61N 1/40; Y10T 307/305; H01F 5/00
See application file for complete search history.

(56) References Cited

U.S. PATENT DOCUMENTS

| 581,206 | A | 4/1897 | Hewitt |
|---|---|---|---|
| 1,898,661 | A | 2/1933 | Hagen |
| 2,035,274 | A | 3/1936 | Mougey |
| 2,297,454 | A | 9/1942 | Berger |
| 2,850,666 | A | 9/1958 | Brewer |
| 3,037,175 | A | 5/1962 | Ruthroff |
| 3,066,295 | A | 11/1962 | Krause |
| 3,519,964 | A | 7/1970 | Chorney |
| 3,588,689 | A | 6/1971 | Crawford |
| 3,683,393 | A | 8/1972 | Self |
| 3,760,812 | A | 9/1973 | Timm |
| 3,774,452 | A | 11/1973 | Tullos |
| 4,131,759 | A | 12/1978 | Felkel |
| 4,229,676 | A | 10/1980 | Manoly |
| 4,266,532 | A | 5/1981 | Ryaby |
| 4,439,702 | A | 3/1984 | Belikov |
| 4,489,276 | A | 12/1984 | Yu |

(Continued)

FOREIGN PATENT DOCUMENTS

| GB | 479841 A | 2/1938 |
|---|---|---|
| GB | 2480610 A | 11/2011 |

(Continued)

*Primary Examiner* — Christine H Matthews
*Assistant Examiner* — Joshua D Lannu
(74) *Attorney, Agent, or Firm* — Sheppard Mullin Richter & Hampton LLP

(57) ABSTRACT

An electrical system including one or more bodies having an underlying structure resembling a double helix may be used to produce useful electromagnetic effects for various applications, including therapy.

72 Claims, 14 Drawing Sheets

(56) References Cited

U.S. PATENT DOCUMENTS

| | | | |
|---|---|---|---|
| 4,832,051 A | 5/1989 | Jarvik |
| 4,989,617 A | 2/1991 | Memberg |
| 5,077,934 A | 1/1992 | Liboff |
| 5,079,458 A | 1/1992 | Schuster |
| 5,173,669 A | 12/1992 | Manoly |
| 5,182,537 A | 1/1993 | Thuis |
| 5,339,061 A | 8/1994 | Reick |
| 5,359,340 A | 10/1994 | Yokota |
| 5,366,493 A | 11/1994 | Scheiner |
| 5,464,456 A | 11/1995 | Kertz |
| 5,654,723 A | 8/1997 | Craven |
| 5,819,467 A | 10/1998 | Zucker |
| 5,851,206 A | 12/1998 | Guglielmi |
| 5,892,480 A | 4/1999 | Killen |
| 5,909,165 A | 6/1999 | Leupold |
| 5,954,630 A | 9/1999 | Masaki |
| 5,977,932 A | 11/1999 | Robinson |
| 6,005,462 A | 12/1999 | Myers |
| 6,169,523 B1 | 1/2001 | Ploussios |
| 6,239,760 B1 | 5/2001 | Van Voorhies |
| 6,300,920 B1 | 10/2001 | Pertl |
| 6,520,986 B2 | 2/2003 | Martin |
| 6,552,530 B1 | 4/2003 | Vaiser |
| 6,770,023 B2 | 8/2004 | Vaiser |
| 6,921,042 B1 | 7/2005 | Goodzeit |
| 6,978,179 B1 | 12/2005 | Flagg |
| 7,148,783 B2 | 12/2006 | Parsche |
| 7,154,368 B2 | 12/2006 | Sweeney |
| 7,375,449 B2 | 5/2008 | Butterfield |
| 8,323,328 B2 | 12/2012 | Martin |
| 8,463,407 B2 | 6/2013 | Bulkes |
| 8,652,023 B2 | 2/2014 | Schmidt |
| 8,653,925 B2 | 2/2014 | Schmidt |
| 8,749,333 B2 | 6/2014 | Schmidt |
| 8,919,035 B2 | 12/2014 | Schmidt |
| 8,961,384 B2 | 2/2015 | Schmidt |
| 9,030,283 B2 | 5/2015 | Schmidt |
| 9,370,667 B2 | 6/2016 | Schmidt |
| 9,406,421 B2 | 8/2016 | Schmidt |
| 9,504,845 B2 | 11/2016 | Schmidt |
| 2003/0011527 A1 | 1/2003 | Kokorin |
| 2003/0158585 A1 | 8/2003 | Burnett |
| 2003/0169132 A1 | 9/2003 | Vaiser |
| 2003/0230427 A1 | 12/2003 | Gareis |
| 2005/0094989 A1 | 5/2005 | Halpin |
| 2005/0121396 A1 | 6/2005 | Kosakewich |
| 2007/0024520 A1 | 2/2007 | Preble |
| 2007/0258329 A1 | 11/2007 | Winey |
| 2008/0161884 A1 | 7/2008 | Chandler |
| 2008/0266203 A1 | 10/2008 | Rossetto |
| 2009/0083969 A1 | 4/2009 | Meinke |
| 2009/0206974 A1 | 8/2009 | Meinke |
| 2009/0260849 A1 | 10/2009 | Cardas |
| 2010/0005711 A1 | 1/2010 | McNeff |
| 2010/0057655 A1 | 3/2010 | Jacobson |
| 2010/0113862 A1 | 5/2010 | Kotowich |
| 2010/0114280 A1 | 5/2010 | Hill |
| 2010/0152811 A1 | 6/2010 | Flaherty |
| 2010/0179630 A1 | 7/2010 | Williams |
| 2012/0101366 A1 | 4/2012 | Ruohonen |
| 2012/0143285 A1 | 6/2012 | Wang |
| 2012/0223800 A1* | 9/2012 | Schmidt .................. H05H 7/04 336/229 |
| 2013/0131537 A1 | 5/2013 | Tam |
| 2013/0192129 A1 | 8/2013 | Schmidt |
| 2013/0211181 A1 | 8/2013 | Schmidt |
| 2013/0285782 A1 | 10/2013 | Schmidt |
| 2014/0097925 A1 | 4/2014 | Schmidt |
| 2014/0100412 A1 | 4/2014 | Schmidt |
| 2014/0218149 A1 | 8/2014 | Schmidt |
| 2014/0371514 A1 | 12/2014 | Schmidt |
| 2015/0119630 A1 | 4/2015 | Schmidt |
| 2015/0119632 A1 | 4/2015 | Schmidt |
| 2015/0157871 A1 | 6/2015 | Schmidt |
| 2015/0283393 A1 | 10/2015 | Schmidt |
| 2015/0283394 A1 | 10/2015 | Schmidt |
| 2016/0172088 A1 | 6/2016 | Schmidt |
| 2016/0172101 A1 | 6/2016 | Schmidt |
| 2016/0247614 A1 | 8/2016 | Schmidt |
| 2016/0247617 A1 | 8/2016 | Schmidt |
| 2016/0365186 A1 | 12/2016 | Schmidt |

FOREIGN PATENT DOCUMENTS

| | | |
|---|---|---|
| WO | 2012118971 A2 | 9/2012 |
| WO | 2013112810 A1 | 8/2013 |
| WO | 2013123009 A1 | 8/2013 |

* cited by examiner

DOUBLE HELIX CONDUCTOR WITH LIGHT EMITTING FLUIDS FOR PRODUCING PHOTOBIOMODULATION EFFECTS IN LIVING ORGANISMS

FIELD OF THE INVENTION

The invention relates to bodies including helically wound runners around which one or more conductive wires or tubes may be wound, devices and/or systems configured to include such bodies. The invention further relates to the manufacture of such bodies and/or devices and/or systems including one or more bodies. The invention further relates to methods of operation of these devices and systems, and applications thereof. The invention further relates to devices and/or systems configured to provide therapy to patients by using electromagnetic effects such as electromagnetic fields.

BACKGROUND OF THE INVENTION

It is known that spirally wound electrical conductors may exhibit certain electromagnetic properties and/or electromagnetic effects. For example, it is known that an electromagnetic coil may act as an inductor and/or part of a transformer, and has many established useful applications in electrical circuits. One or more electromagnetic coils may be used to exploit an electromagnetic field and/or other electromagnetic effect that is created when, e.g., one or more active current sources are operatively coupled to the one or more coils.

SUMMARY

One aspect of the invention relates to a system comprising one or more bodies, one or more current sources, one or more pumps, one or more tubes, and/or one or more conductive wires. Individual bodies may include two intertwined helically wound runners. A first runner may be coupled to the second runner by struts. Individual runners may have a helical shape. Individual bodies may be arranged in toroidal shapes. One or more conductive wires and/or tubes may be spirally wound around at least one runner. One or more runners and/or tubes may include material that is non-porous to liquid. One or more runners and/or tubes may include material that is translucent and/or transparent. One or more runners and/or tubes may be configured to carry liquid that emits electromagnetic radiation.

These and other objects, features, and characteristics of the present disclosure, as well as the methods of operation and functions of the related components of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the any limits. As used in the specification and in the claims, the singular form of "a", "an", and "the" include plural referents unless the context clearly dictates otherwise.

DETAILED DESCRIPTION

Figure 1:
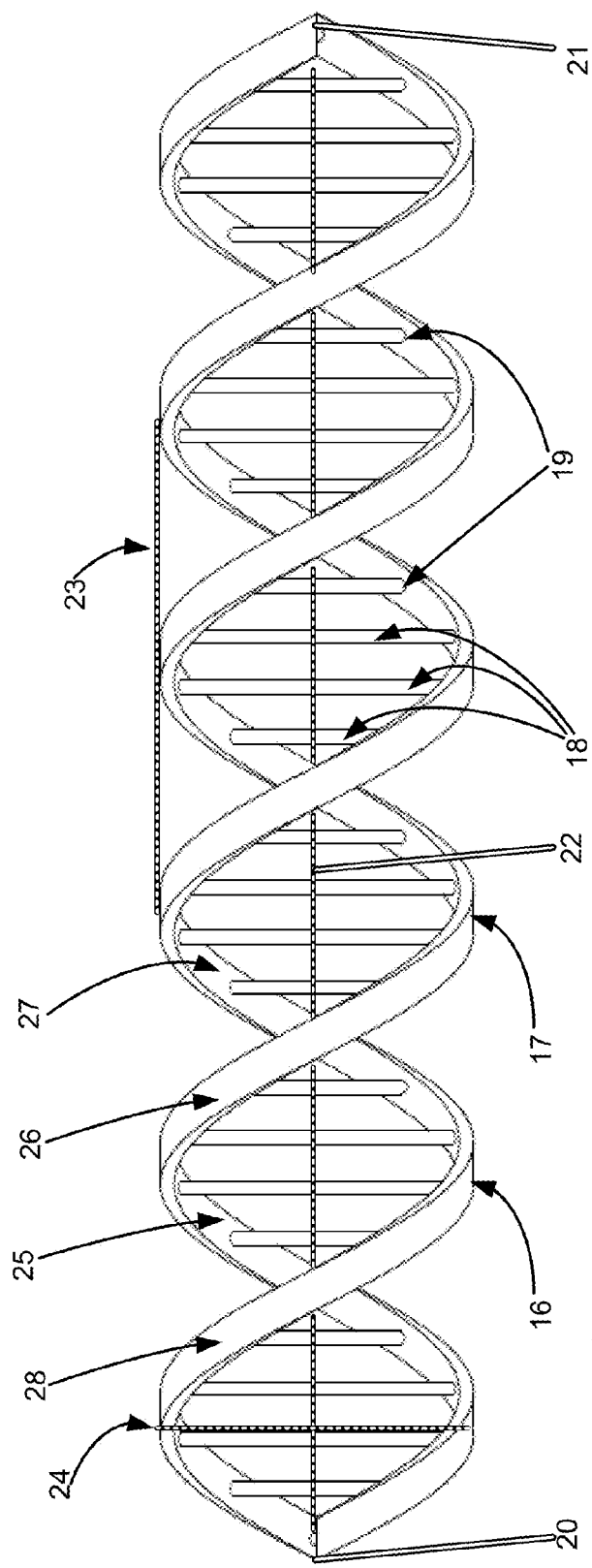
FIG. 1 illustrates a side view of an exemplary body including two intertwined helically wound runners, coupled by struts.

FIG. 1 illustrates a side view of an exemplary body 15. Body 15 may include two or more intertwined helically wound runners—runner 16 and runner 17. Runner 16 and runner 17 may be coupled by struts 18. Body 15 includes two ends—end 20 and end 21—disposed at opposite sides of body 15. Runners 16 and/or 17 may be arranged in the shape of a three-dimensional curve similar to or substantially the same as a helix. A helix may be characterized by the fact that a tangent line at any point along the curve has a constant angle with a (fixed) line called the axis. The pitch of a helix may be the width of one 360 degree helix turn (a.k.a. revolution), e.g. measured parallel to the axis of the helix. Intertwined helically wound runners may share the same axis, be congruent, and/or differ by a translation along the axis, e.g. measuring half the pitch. The two runners shown in FIG. 1 may share the same axis 22, extending horizontally for approximately three complete revolutions. The length of body 15, as measured along axis 22 from end 20 to end 21, may thus be approximately three times the length of pitch 23. A helical shape may have constant pitch, constant radius (measured in the plane perpendicular to the axis), constant torsion, constant curvature, constant ratio of curvature to torsion, and/or a straight axis. In FIG. 1, the radius of body 15 may be half of diameter 24. It is noted that the shape of body 15 resembles the general shape of deoxyribonucleic acid (DNA).

By way of non-limiting example, additional structures and/or features of body 15 may be described in U.S. Pat. No. 8,653,925, entitled "Double Helix Conductor," which issued Feb. 18, 2014, which is hereby incorporated into this disclosure by reference in its entirety. This patent may also be referred to as "the '925 patent" herein.

In FIG. 1, the shape of cross-section of runner 16 and runner 17 may be a rectangle that is approximately three times wider than it is tall. Furthermore, the width of runner 16 or runner 17 may be approximately $\frac{1}{13}^{th}$ of the pitch of said runner of body 15. As a result, runner 17 of body 15 resembles a ribbon having an inner surface 25 (facing axis 22 of the helical shape) and an outer surface 26 (facing the opposite way as inner surface 25). Runner 16 of body 15 resembles a ribbon having an inner surface 27 (facing axis 22 of the helical shape) and an outer surface 28 (facing the opposite way as inner surface 27). Note that embodiments of this disclosure are not intended to be limited by any of the given examples.

Runner 16, runner 17 and/or struts 18 may be manufactured from one or more of plastic, plastic plated with metals including copper, nickel, iron, soft iron, nickel alloys, and/or other metals and alloys, and/or other materials. In some embodiments, runner 16, runner 17 and struts 18 are manufactured from non-conductive material. Runner 16, runner 17, and/or struts 18 may be manufactured from different materials.

In some embodiments, runner 16, runner 17 and struts 18 may include material that is non-porous to liquid. In some embodiments, runner 16, runner 17 and struts 18 may include material that is translucent and/or transparent.

Runner 16, runner 17, and/or struts 18 may be manufactured through integral construction or formed separately prior to being assembled. In some embodiments, runner 16, runner 17, and/or struts 18 may be include magnetically permeable material. In some embodiments, runner 16, runner 17, and/or struts 18 may be include non-ferromagnetic yet conducting material.

In some embodiments, runners 16 and/or 17 may be at least partially hollow. In some embodiments, runners 16 and/or 17 may include one or more cavities spanning the runners longitudinally. In some embodiments, runners 16 and/or 17 may be configured such that fluid can flow through one or both runners.

Figure 2:
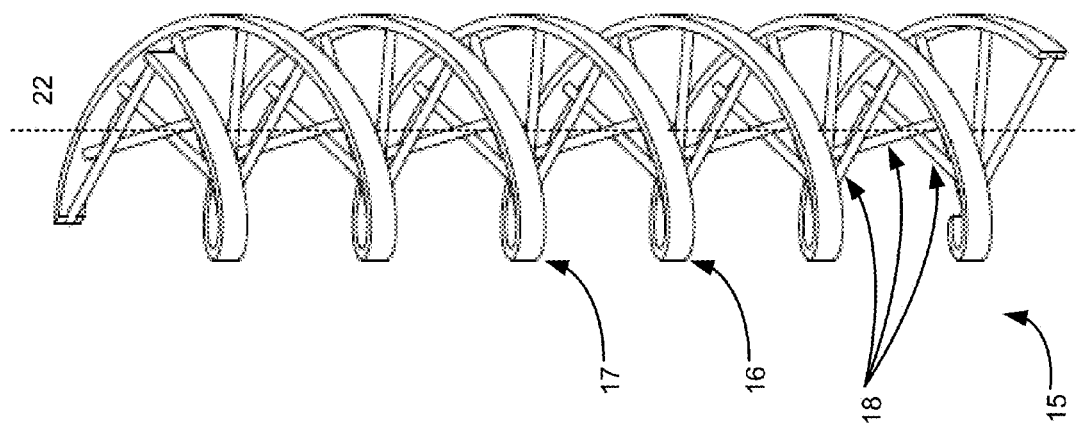
FIG. 2 illustrates an isometric view of an exemplary body including two intertwined helically wound runners, coupled by struts.

FIG. 2 illustrates an isometric view of an exemplary body 15 including two intertwined helically wound runners—runner 16 and runner 17—coupled by struts 18. Body 15 is shown here with axis 22 of both helically wound runners extending vertically.

Figure 3:
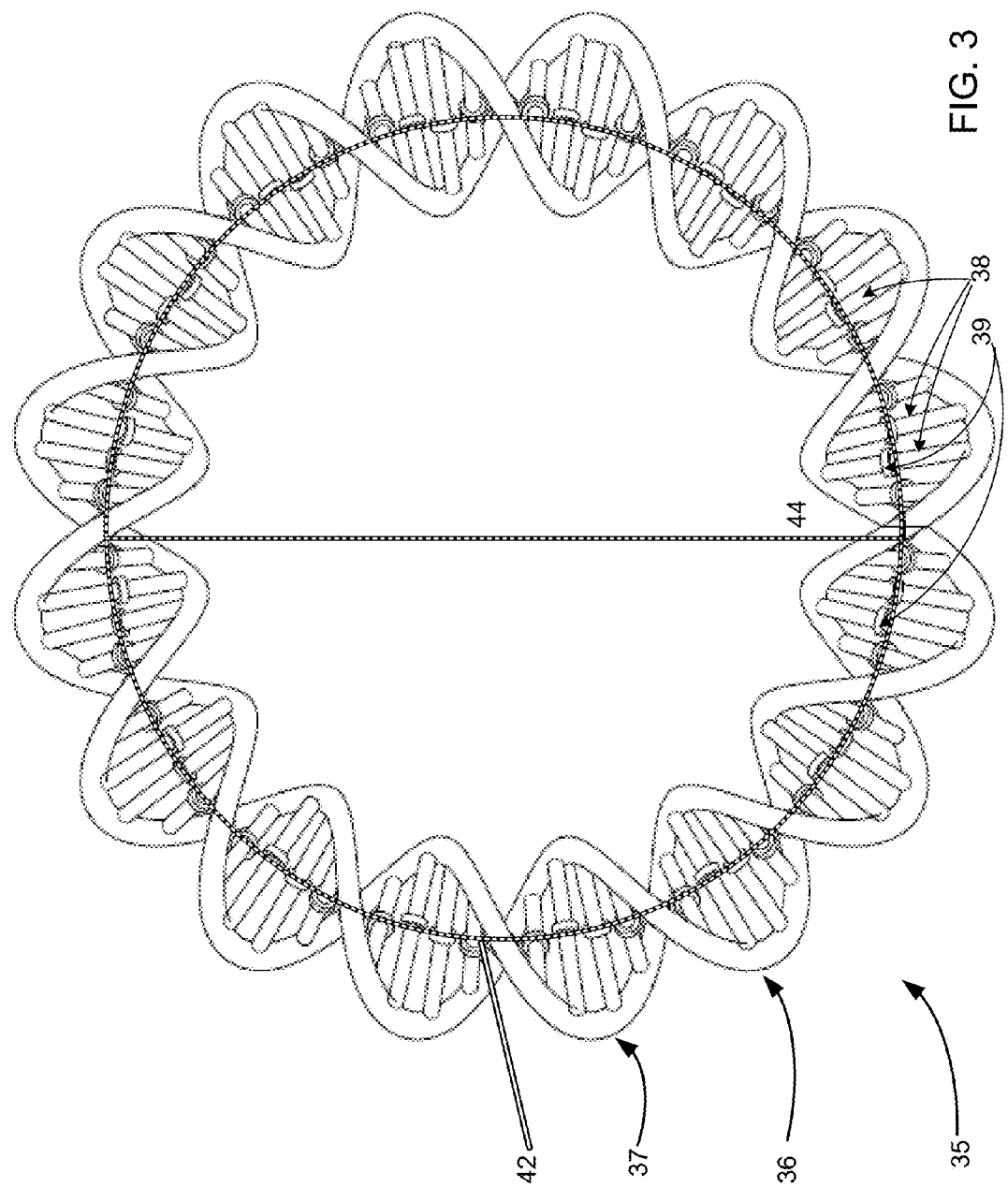
FIG. 3 illustrates a top-down view of an exemplary body including two intertwined helically wound runners sharing the same circular axis, both runners coupled by struts.

FIG. 3 illustrates a top-down view of an exemplary body 35 including two intertwined helically wound runners—runner 36 and runner 37—sharing the same circular axis 42, both runners coupled by struts 38. The resulting shape of body 35 may be referred to as toroidal. Body 35 may be formed the same as or similar to body 15, though comprising more revolutions, by arranging the body in a planar circular shape and joining both ends—end 20 and end 21 in FIG. 1—together. The preceding statement is not intended to limit the (process of) manufacture of bodies similar to or substantially the same as body 35 in any way.

Referring to FIG. 3, the diameter 44 of the circular axis of body 35, as well as the number of complete revolutions per runner required to completely extend along the entire circular axis 42 may be characteristic measurements/features of body 35. For example, as shown in FIG. 3, runner 36 and runner 37 of body 35 may require approximately eight complete revolutions around circular axis 42 to completely extend along the entire circular axis 42 of body 35, or some other number of rotations.

Note that one or more struts 38 of body 35 in FIG. 3 include a center-strut element 39, which is lacking from struts 18 of body 15. Center-strut element 39 may be associated with a particular strut of body 35.

In some embodiments, runners 36 and 37 as depicted in FIG. 3 may share one or more features attributed to runners 16 and 17 in FIGS. 1 and 2. For example, runners 36 and 37 in FIG. 3 may include material that is translucent and/or transparent. In some embodiments, runners 36 and/or 37 may be at least partially hollow. In some embodiments, runners 36 and/or 37 may include one or more cavities spanning the runners longitudinally. In some embodiments, runners 36 and/or 37 may be configured such that fluid can flow through one or both runners.

Figure 4:
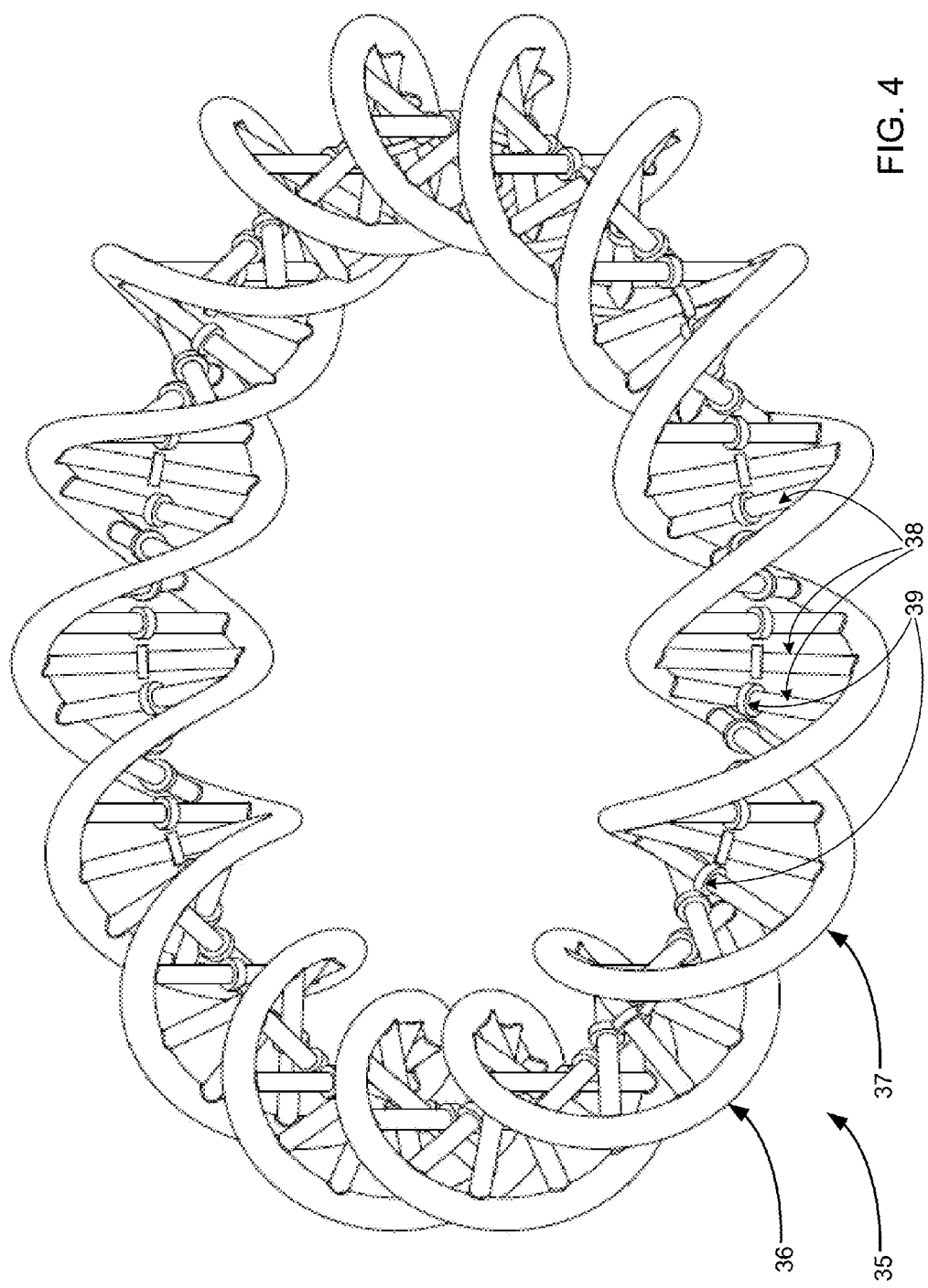
FIG. 4 illustrates an isometric view of an exemplary body including two intertwined helically wound runners sharing the same circular axis, both runners coupled by struts.

FIG. 4 illustrates an isometric view of an exemplary body 35 including two intertwined helically wound runners—runner 36 and runner 37—sharing the same circular axis, both runners coupled by struts 38. Note that, as in FIG. 3, the struts of body 35 in FIG. 4 may include a center-strut element 39, which may be lacking from struts 18 of body 15.

Figure 5:
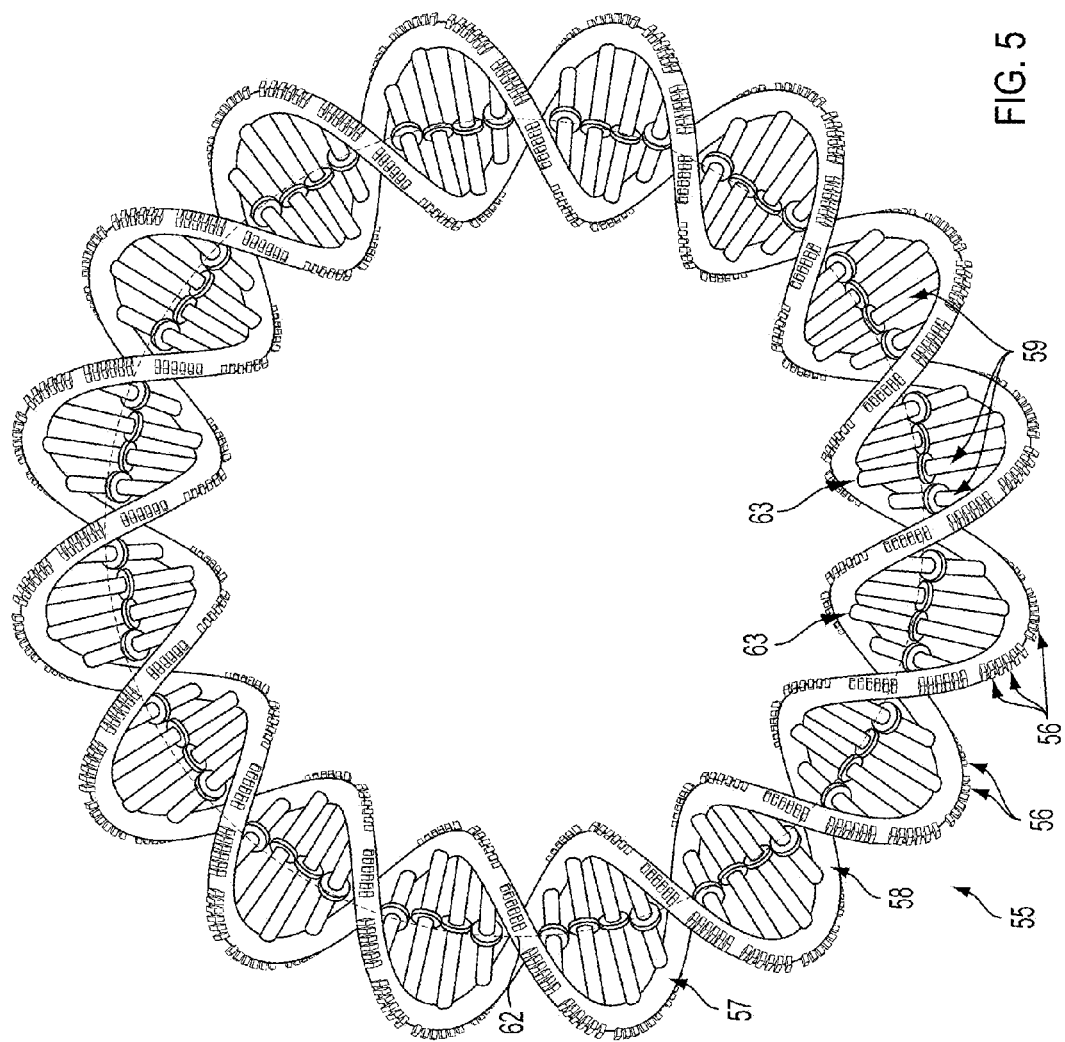
FIG. 5 illustrates a top-down view of an exemplary body including two intertwined helically wound runners sharing the same circular axis and having wire guides, both runners coupled by struts.

FIG. 5 illustrates a top-down view of an exemplary body 55 including two intertwined helically wound runners—runner 57 and runner 58—sharing the same circular axis 62 and having wire guides 56, both runners coupled by struts 59. Any part of runner 57 or runner 58 may include wire guides 56. Wire guides 56 may include grooves, notches, protrusions, slots, and/or other structural elements disposed on and/or in runner 57 or runner 58 and configured to guide a wire or tube along at least a part of the surface of runner 57 or runner 58.

Such a wire, as any wire listed in any figure included in this description, may be insulated, uninsulated, or partially insulated and partially uninsulated. As used herein, a "wire" may include a set of twisted wires (which may interchangeably be referred to as a "twisted wire"), including but not limited to a set of two twisted wires. The number of turns of a set of twisted wires per inch and/or per helical revolution of a runner may be characteristic measurements/features of the system. In some embodiments, the number of twists per inch of a twisted wire may be about 2, about 5, about 10, about 20, about 100, and/or another suitable number of twists. In some embodiments, the frequency characteristics of an alternating current and/or the corresponding generated electromagnetic field may be based on, proportional to, and/or otherwise related to the number of twists of a twisted wire. For example, a higher number of twists per inch may correspond to a higher operating frequency for the alternating current and/or the corresponding generated electromagnetic field. In some embodiments, multiple twisted wires (e.g. a first twisted wire wound around a first runner and a second twisted wire wound around a second runner) may have the same direction of twisting, and/or a different direction of twisting. In some embodiments, multiple wires (e.g. twisted wires) may be wound around the same runner. In some embodiments, a wire may be wound around some or all of one or more struts.

In some embodiments, one or more tubes (not depicted in FIG. 5) may be guided around runner 57 and/or runner 58 by wire guides 56.

Figure 6:
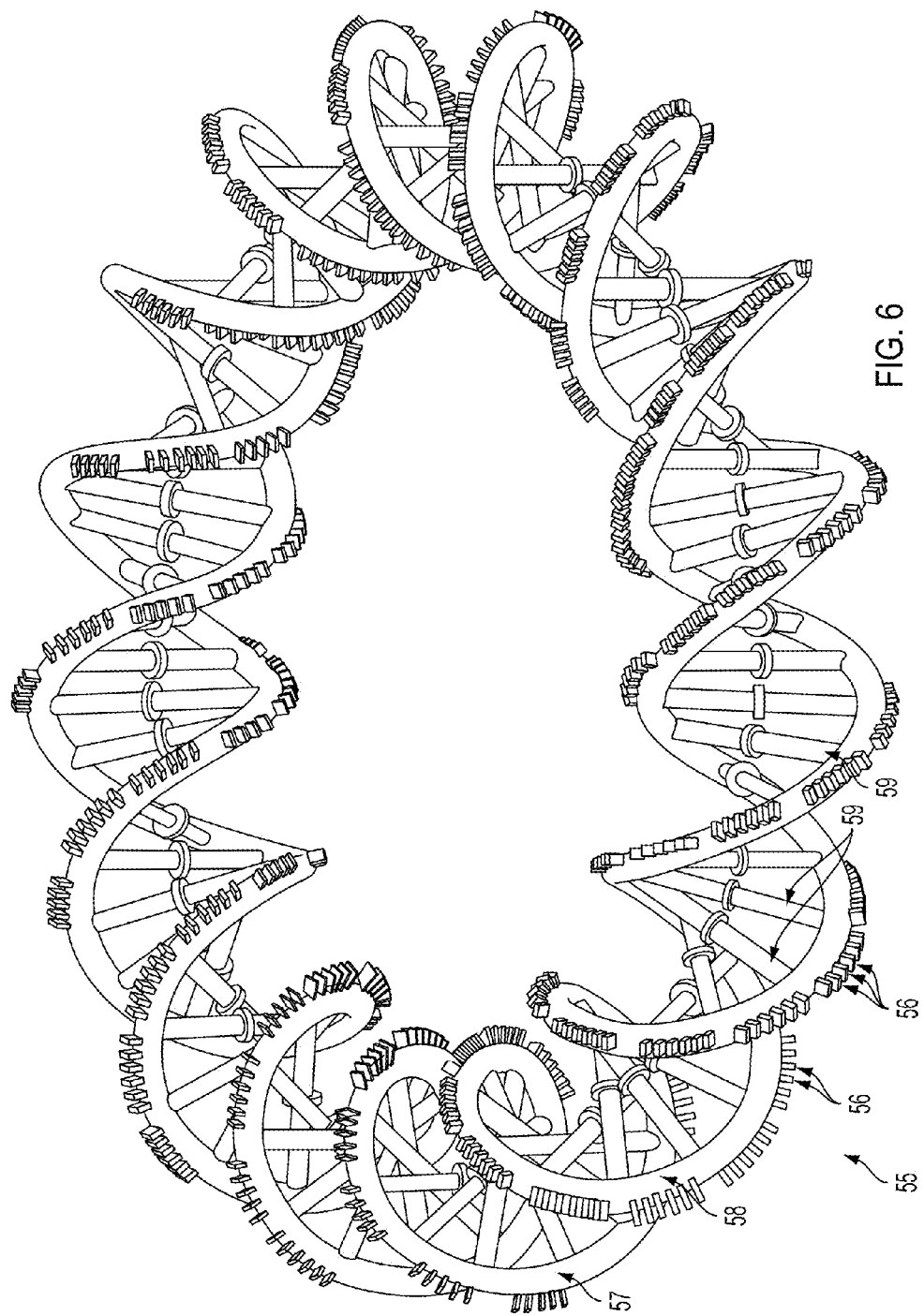
FIG. 6 illustrates an isometric view of an exemplary body including two intertwined helically wound runners sharing the same circular axis and having wire guides, both runner coupled by struts.

FIG. 6 illustrates an isometric view of an exemplary body 55 including two intertwined helically wound runners—runner 57 and runner 58—sharing the same circular axis and having wire guides 56, both runners coupled by struts 59.

Figure 7:
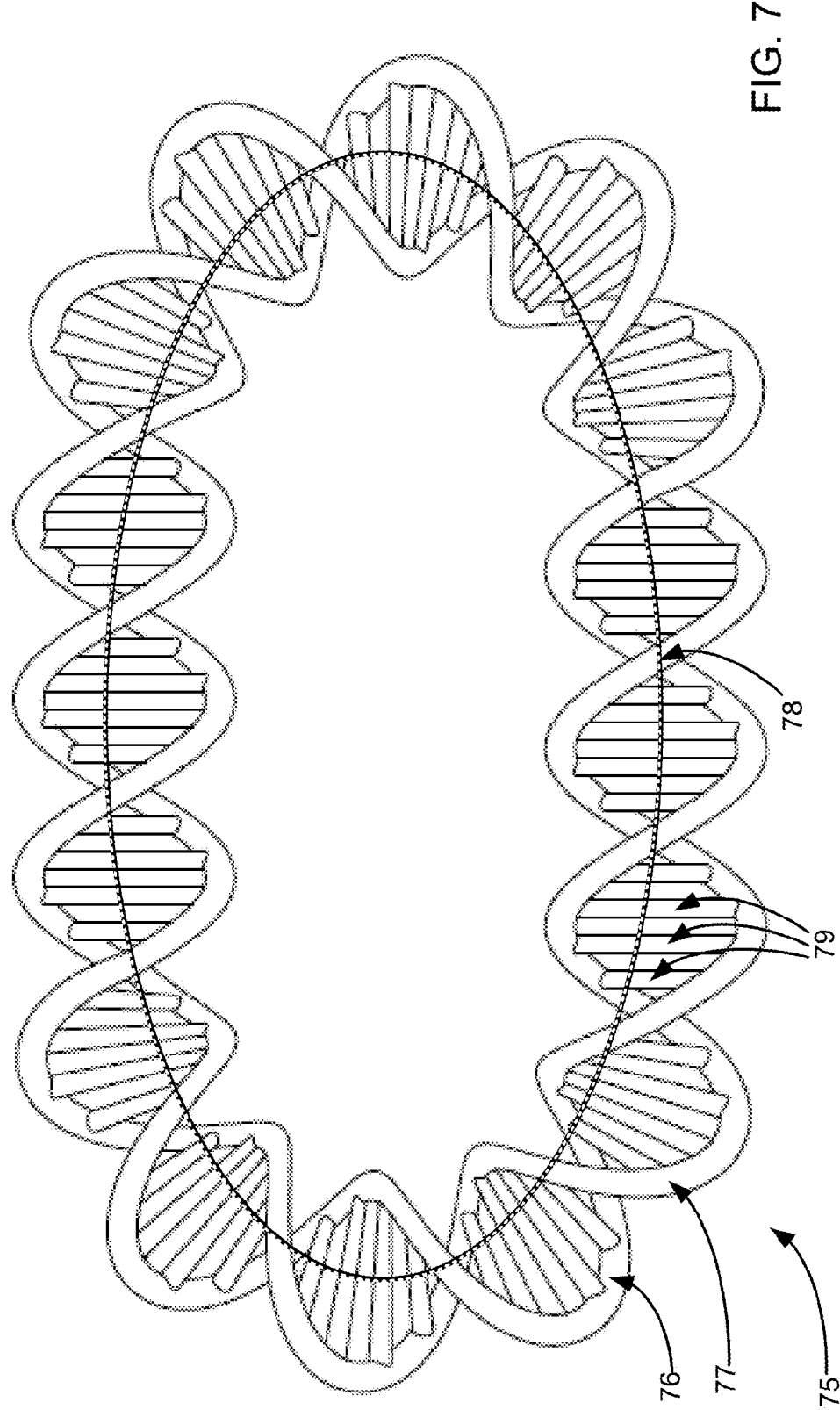
FIG. 7 illustrates an exemplary body including two intertwined helically wound runners sharing the same elliptical axis, both runner coupled by struts.

FIG. 7 illustrates an exemplary body 75 including two intertwined helically wound runners—runner 76 and runner 77—sharing the same elliptical axis 78, both runner coupled by struts 79. A body including two (or more) intertwined helically wound runners sharing the same axis may be arranged in any planar shape, including a circle, an oval, a triangle, a square, a rectangle, an angular shape, a polygon, and/or other planar shapes. Alternatively, and/or simultaneously, such a body may be arranged in a three-dimensional curve (a.k.a. space curve). In FIG. 7, body 75 may be formed from a body similar to body 15, though comprising more revolutions, by arranging the body in a planar elliptical shape and joining both ends—end 20 and end 21 in FIG. 1—together. The preceding statement is not intended to limit the (process of) manufacture of bodies similar to or substantially the same as body 75 in any way.

In some embodiments, runners 76 and 77 as depicted in FIG. 7 may share one or more features attributed to runners 16 and 17 in FIGS. 1 and 2, and/or runners 36 and 37 in FIGS. 3 and 4. For example, runners 76 and 77 in FIG. 7 may include material that is translucent and/or transparent. In some embodiments, runners 76 and/or 77 may be at least partially hollow. In some embodiments, runners 76 and/or 77 may include one or more cavities spanning the runners longitudinally. In some embodiments, runners 76 and/or 77 may be configured such that fluid can flow through one or both runners.

Figure 8:
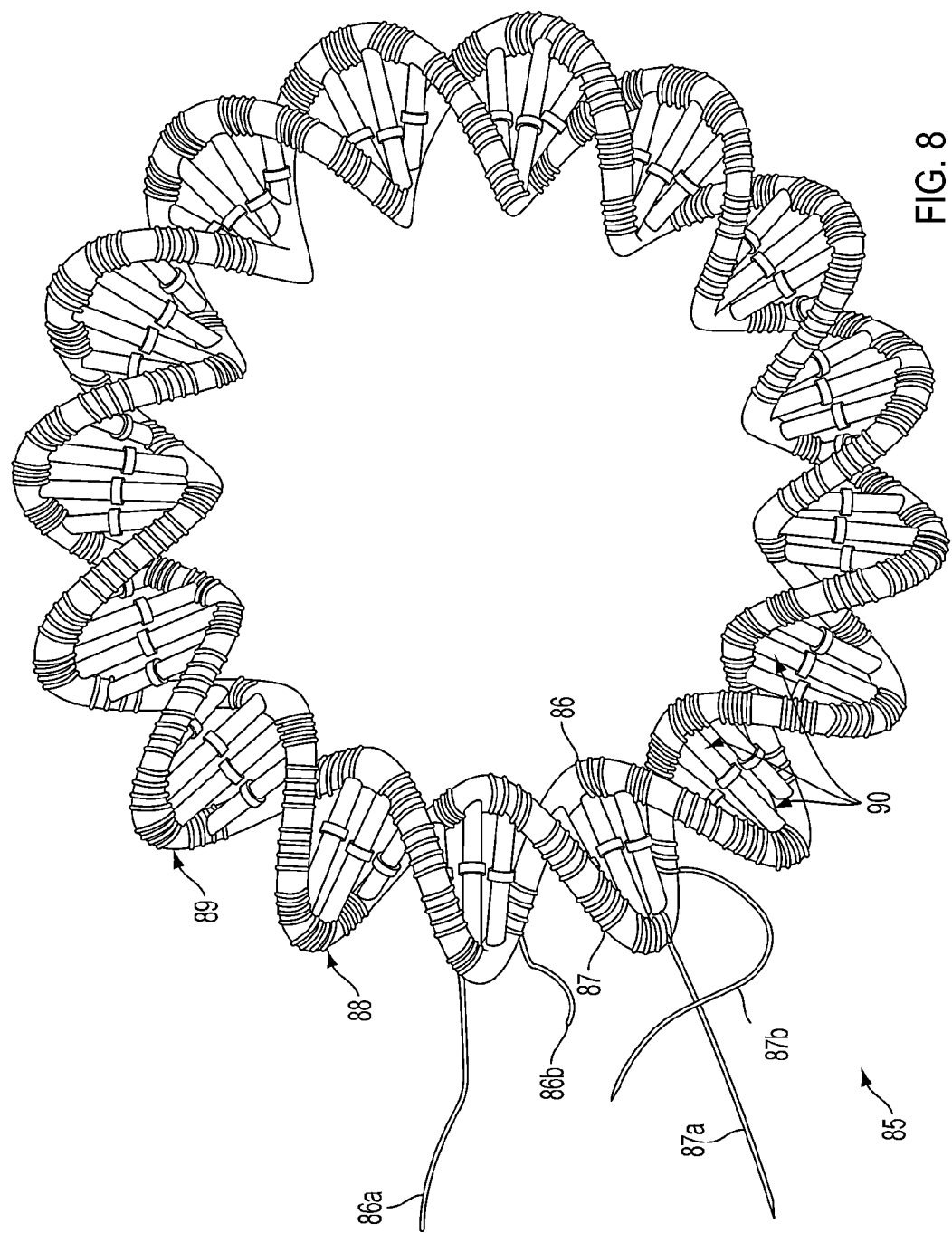
FIG. 8 illustrates a top-down view of an exemplary body including two intertwined helically wound runners sharing the same circular axis, both runners coupled by struts and having conductive wires spirally wound therearound.

FIG. 8 illustrates a top-down view of an exemplary body 85 including two intertwined helically wound runners—runner 88 and runner 89—sharing the same circular axis, coupled by struts 90 and having wires—wire 86 and wire 87—spirally wound therearound. In some embodiments, wire 86 and/or wire 87 may be conductive wires. In some embodiments, wire 86 and/or wire 87 may be tubes. Wire 86 and/or wire 87, as any wire listed in any figure included in this description, may be insulated, uninsulated, or partially insulated and partially uninsulated. Wire 86 and/or wire 87, as any wire listed in any figure included in this description, may be a twisted wire. Runner 88 and runner 89 of body 85 may form cores around which wire 86 and wire 87 are spirally wound, respectively. As such, wire 86 and wire 87 may be arranged in a helical shape having axes that coincide with runner 88 and runner 89, respectively.

In some embodiments, runners 88 and 89 as depicted in FIG. 8 may share one or more features attributed to runners 16 and 17 in FIGS. 1 and 2, and/or runners 36 and 37 in FIGS. 3 and 4, and/or runners 76 and 77 in FIG. 7. For example, runners 88 and 89 in FIG. 8 may include material that is translucent and/or transparent. In some embodiments, runners 88 and/or 89 may be at least partially hollow. In some embodiments, runners 88 and/or 89 may include one or more cavities spanning the runners longitudinally. In some embodiments, runners 88 and/or 89 may be configured such that fluid can flow through one or both runners.

Wire 86 may include two leads—lead 86a and lead 86b. Wire 87 may include two leads—lead 87a and lead 87b. Wire 86 and wire 87 may be conductive. One or more bodies similar to or the same as body 85 may be used in an electrical system having one or more power sources and/or current sources arranged such that electrical coupling with one or both of wire 86 and wire 87 may be established, e.g. through coupling with lead 86a and 86b of wire 86 and through coupling with lead 87a and 87b of wire 87. The current supplied to wire 86 may be a direct current or an alternating current. The current supplied to wire 87 may be a direct current or an alternating current. The currents supplied to wire 86 and wire 87 may flow in the same direction or the opposite direction. For alternating currents, operating frequencies ranging from 0 Hz to 40 GHz are contemplated. The operating frequencies for wire 86 and wire 87 may be the same or different. Other electrical operating characteristics of current supplied to wire 86 and wire 87, such as phase, amplitude, power-level, and/or other operating characteristics, may be the same or different. The electrical system may be used to exploit the electromagnetic field that is created when electrical power is supplied to one or more wires of one or more bodies similar to or the same as body 85.

Figure 9:
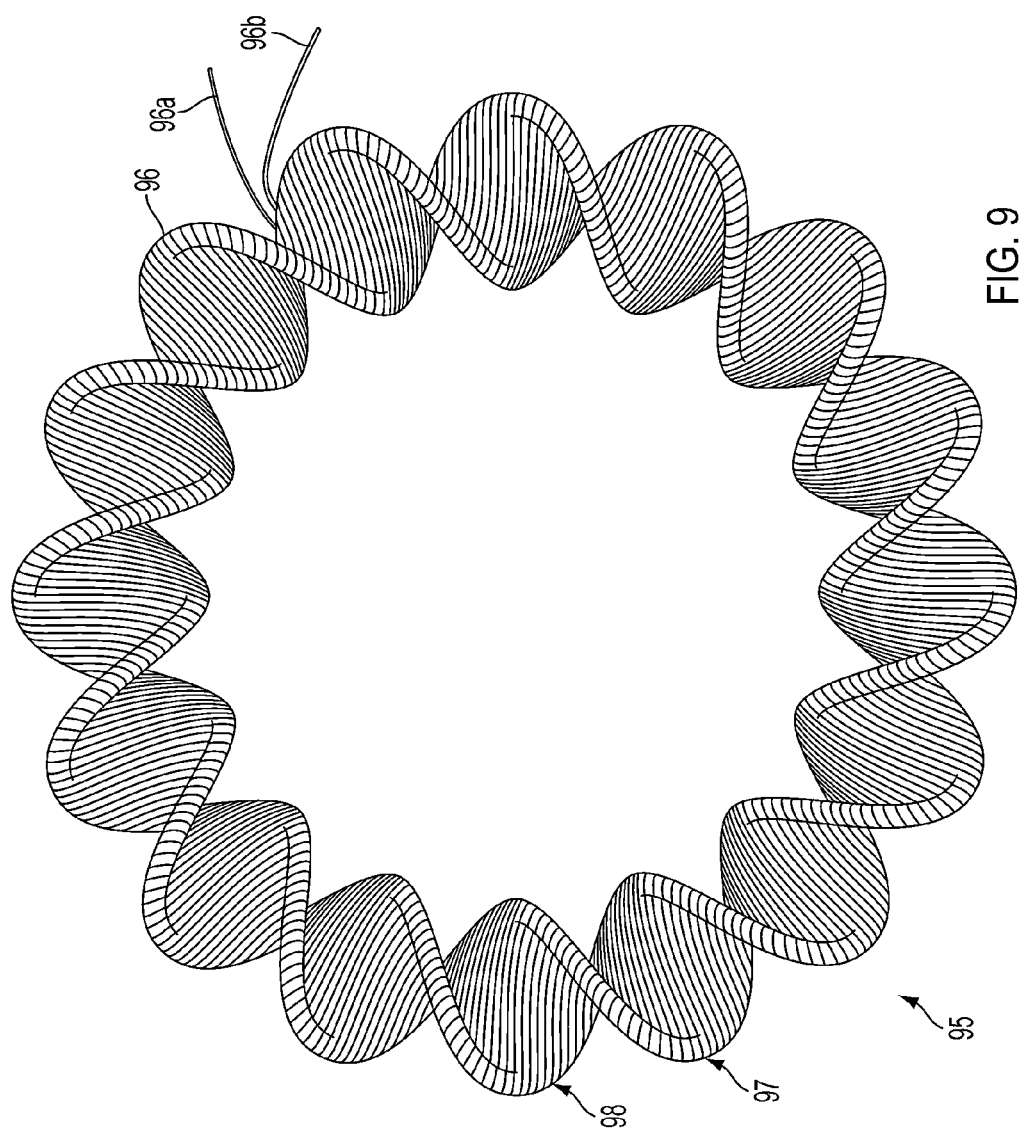
FIG. 9 illustrates a top-down view of an exemplary body including two intertwined helically wound runners sharing the same circular axis, both runner coupled by struts and having a wire spirally wound around both runners of the body.

FIG. 9 illustrates a top-down view of an exemplary body 95 including two intertwined helically wound runners—runner 97 and runner 98—sharing the same circular axis, both runner coupled by struts and having a wire 96 spirally wound around both runners of body 95. Wire 96 may include two leads—lead 86a and lead 86b. The resulting shape of body 95 with wire 96 may be referred to as a helicoidal shape. One or more bodies similar to or the same as body 95 may be used in an electrical system having a power source and/or a current source arranged such that electrical coupling with wire 96, e.g. through leads 96a and 96b, may be established. The electrical power supplied to wire 96 may include a direct current or an alternating current. Operating frequencies for an alternating current flowing through wire 96 are contemplated to range from 0 Hz to 40 GHz. The electrical system may be used to exploit the electromagnetic field that is created when electrical power is supplied.

In some embodiments, runners 97 and 97 as depicted in FIG. 9 may share one or more features attributed to runners 16 and 17 in FIGS. 1 and 2, and/or runners 36 and 37 in FIGS. 3 and 4, and/or runners 76 and 77 in FIG. 7, and/or runners 88 and 89 in FIG. 8. For example, runners 97 and 98 in FIG. 9 may include material that is translucent and/or transparent. In some embodiments, runners 97 and/or 98 may be at least partially hollow. In some embodiments, runners 97 and/or 98 may include one or more cavities spanning the runners longitudinally. In some embodiments, runners 97 and/or 98 may be configured such that fluid can flow through one or both runners.

Figure 10:
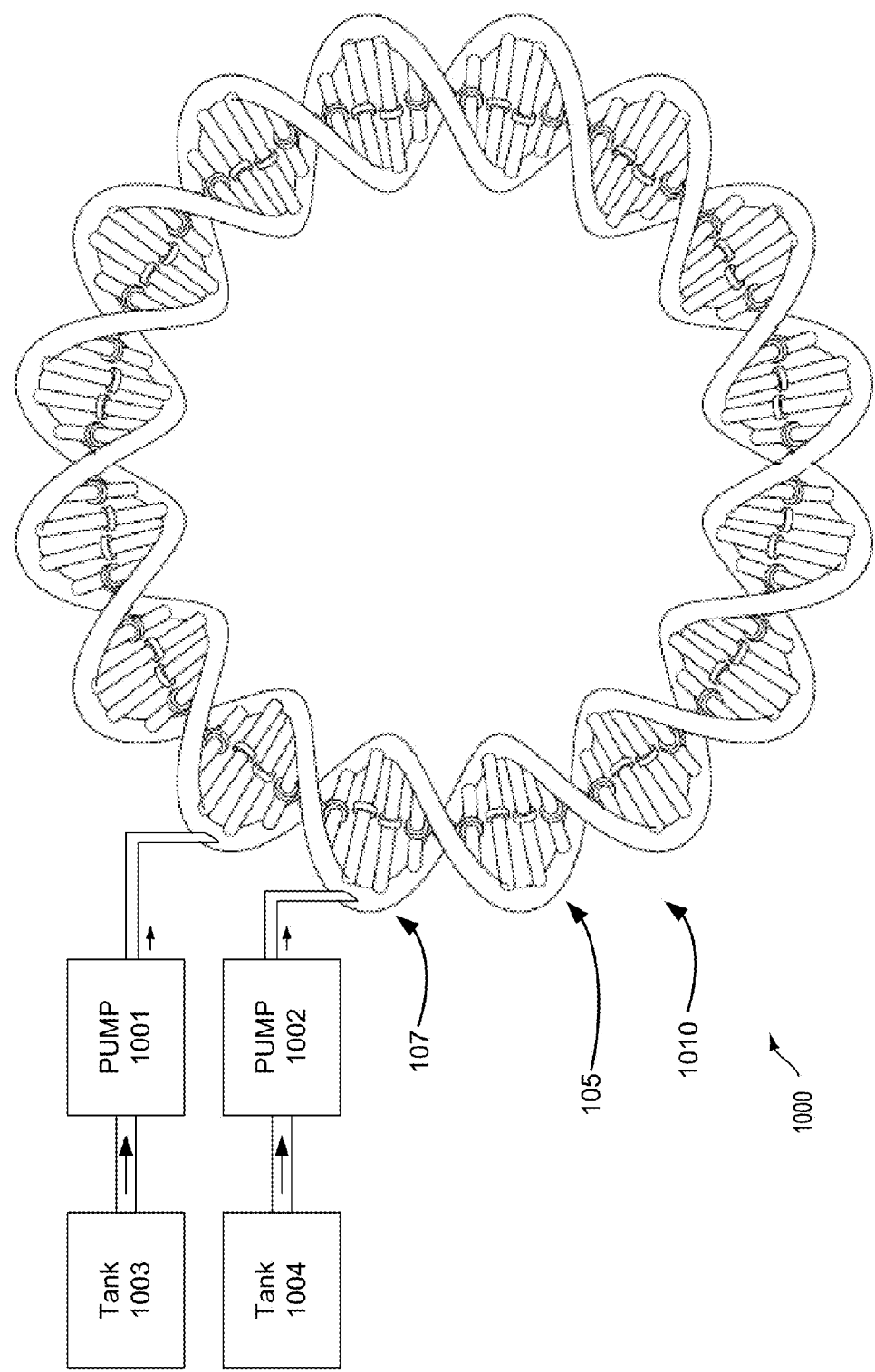
FIGS. 10 and 11 illustrate top-down views of exemplary systems combining a body with one or more pumps.

FIG. 10 illustrates a top-down view of exemplary system 1000 that combines a body 1010 with one or more pumps, one or more tanks, and/or other components. Body 1010 includes two intertwined helically wound runners, runner 105 and runner 107, sharing the same circular axis in a similar manner as depicted in FIG. 3. Runners 105 and 107 in FIG. 10 may include material that is translucent and/or transparent. In some embodiments, runners 105 and/or 107 may be at least partially hollow. In some embodiments, runners 105 and/or 107 may include one or more cavities spanning the runners longitudinally. In some embodiments, runners 105 and/or 107 may be configured such that fluid can flow through one or both runners.

Tank 1003 and tank 1004 may be configured to hold liquid. Tank 1003 may be operatively coupled to pump 1001. Tank 1004 may be operatively coupled to pump 1002. Pump 1001 may be operatively coupled to runner 105. Pump 1002 may be operatively coupled to runner 107. In some embodiments, one or more of pump 1001 and pump 1002 may be configured to pump liquid along runner 105 and/or runner 107, e.g. through cavities within runner 105 and/or runner 107. In some embodiments, one or more of pump 1001 and pump 1002 may be configured to pump liquid along runner 105 and/or runner 107 in a particular direction. In some embodiments, liquid may be pumped, within runner 105, in a different direction compared to runner 107. In some embodiments, a single pump may be configured to pump liquid through runner 105 and runner 107. In some embodiments, a single tank may be configured to hold liquid used to pump through runner 105 and runner 107.

The liquid pumped by pump 1001 and/or pump 1002 may emit electromagnetic radiation. For example, liquid pumped through runner 105 may emit electromagnetic radiation through translucent and/or transparent material included in runner 105. By virtue of using specific wavelengths, emitted electromagnetic radiation may produce specific biological effects. This biophysical principle may be referred to as photobiomodulation. In some embodiments, the liquid pumped by pump 1001 and/or pump 1002 may interact with a flow of energy of a subject. In some embodiments, the liquid pumped by pump 1001 and/or pump 1002 may include a measurable amount and/or concentration of left-handed molecules. In some embodiments, the liquid pumped by pump 1001 and/or pump 1002 may include a measurable amount and/or concentration of right-handed molecules. In some embodiments, left-handed molecules and/or right-handed molecules may include stereoisomers. In some embodiments, left-handed molecules and/or right-handed molecules may be selected from a set of stereoisomers and/or other compounds. The set of stereoisomers and compounds may include one or more of L-Alanine, L-Arginine, L-Aspargine, L-Aspartic Acid, L-Carnitine, Acetyl-L-Carnitine, L-Carnitine L-Tartrate, L-Carnitine Magnesium Citrate, L-Citrulline, L-Cysteine, L-Cystine, L-GABA, L-Glutamic Acid, L-Glutamine, Glutathione Peroxidase, L-Glycine, L-Histidine, Hydroxyglutamic Acid, Hydroxyproline, L-Isoleucine, L-Leucine, Norleucine, L-Lysine, L-Methionine, L-Ornithine, L-Valine, L-Phenylalanine, L-Proline, L-Serine, L-Taurine, L-Threonine, L-Tryptophan, L-Tyrosine, D-Alanine, D-Arginine, D-Aspargine, D-Aspartic Acid, D-Carnitine, Acetyl-D-Carnitine, D-Carnitine D-Tartrate, D-Carnitine Magnesium Citrate, D-Citrulline, D-Cysteine, D-Cystine, D-GABA, D-Glutamic Acid, D-Glutamine, D-Glutathione Peroxidase, D-Glycine, D-Histidine, D-Hydroxyglutamic Acid, D-Hydroxyproline, D-Soleucine, D-Leucine, D-Norleucine, D-Lysine, D-Metbionine, D-Ornithine, D-Valine, D-Phenylalanine, D-Proline, D-Serine, D-Taurine, D-Threonine, D-Tryptophan, D-Tyrosine, dextrin, dextrose, fructose, galactose, glucose, glycogen, inositol, invert sugar, lactose, levulose, maltose, molasses, sucrose, xylose, high fructose corn syrup, honey, molasses, and/or sugar cane.

Proximity of these stereoisomers and compounds to a human body may produce desirable biological effects. Any combination of a generated electromagnetic effect (e.g. an electromagnetic field generated as described in this disclosure), emitted electromagnetic radiation, and/or biological effects produced by virtue of proximity (as described in this disclosure) may be used to provide therapy to a subject.

In some embodiments, one or both runners of body 1010 may be spirally wound using one or more conductive wires (not shown) in a manner similar to descriptions elsewhere in this disclosure. For example, one or both runners of body 1010 may be spirally wound using one or more conductive wires such that, responsive to one or more alternating currents being provided to the one or more conductive wires, an electromagnetic effect may be generated, including but not limited to an electromagnetic field.

Figure 11:
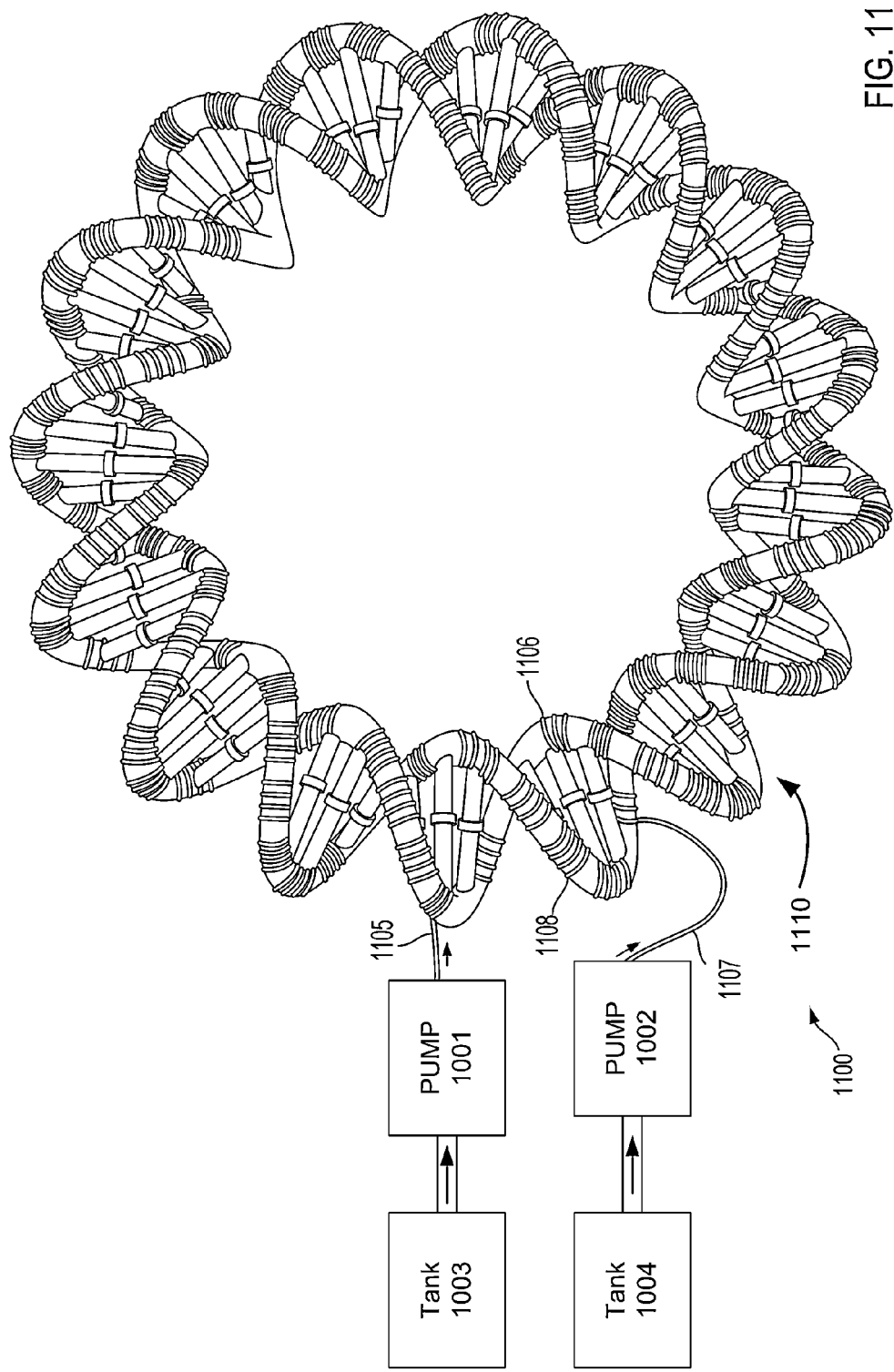

FIG. 11 illustrates a top-down view of exemplary system 1100 that combines a body 1110 with one or more pumps, one or more tanks, one or more tubes, and/or other components. Body 1110 includes two intertwined helically wound runners, runner 1106 and runner 1108, sharing the same circular axis in a similar manner as depicted in FIG. 8. Body 1110 may include tubes 1105 and/or 1107. Tube 1105 may be spirally wound around runner 1106. Tube 1107 may be spirally wound around runner 1108. Runners 1106 and 1108 and/or tubes 1105 and 1107 in FIG. 10 may include material that is translucent and/or transparent. In some embodiments, runners 1106 and 1108 and/or tubes 1105 and 1107 may be at least partially hollow. In some embodiments, runners 1106 and 1108 and/or tubes 1105 and 1107 may include one or more cavities spanning the runners longitudinally. In some embodiments, runners 1106 and 1108 and/or tubes 1105 and 1107 may be configured such that fluid can flow through one or both runners.

Tank 1003 and tank 1004 may be configured to hold liquid. Tank 1003 may be operatively coupled to pump 1001. Tank 1004 may be operatively coupled to pump 1002. Pump 1001 may be operatively coupled to tube 1105. Pump 1002 may be operatively coupled to tube 1107. In some embodiments, one or more of pump 1001 and pump 1002 may be configured to pump liquid through tube 1105 and/or tube 1107. In some embodiments, one or more of pump 1001 and pump 1002 may be configured to pump liquid through tube 1105 and/or tube 1107 in a particular direction. In some embodiments, liquid may be pumped, within tube 1105, in a different direction compared to tube 1107. In some embodiments, a single pump may be configured to pump liquid through tube 1105 and tube 1107. In some embodiments, a single tank may be configured to hold liquid used to pump through tube 1105 and tube 1107.

In some embodiments, one or both runners of body 1110 and/or one or both tubes of body 1110 may be spirally wound using one or more conductive wires (not shown) in a manner similar to descriptions elsewhere in this disclosure. For example, one or both runners of body 1010 and/or one or both tubes of body 1110 may be spirally wound using one or more conductive wires such that, responsive to one or more alternating currents being provided to the one or more conductive wires, an electromagnetic effect may be generated, including but not limited to an electromagnetic field.

Any of the bodies and/or systems shown in FIGS. 1-11 may be used in an electrical system. Conductive wires may be spirally wound around one or more runners, one or more struts, and/or any combination thereof to produce electrical systems having specific electromagnetic properties when electrical power is supplied to one or more of the conductive wires.

Applications for any of the electrical systems described herein may include affecting growth and/or growth rate of plants and/or other organisms, medical applications, therapeutic applications, energy production, energy conversion, energy transformation, adenosine triphosphate (ATP) production, ATP transfer, ATP processing, and/or other applications.

In some embodiments, an electrical system including any of the bodies shown in FIGS. 1-11 (and/or multiple instances thereof) may be used as a component in an electrical circuit, performing one or more functions and/or applications including a (tunable) inductor, a (Tesla) coil, a transformer, a transducer, a transistor, a resistor, a solenoid, a stator for an electrical motor, an electromagnet, an electromagnetic pulse generator, an electromagnetic actuator, an energy conversion device, a position servomechanism, a generator, a stepping motor, a DC motor, a (contact-free) linear drive, an axial flux device, a measurement device for magnetic permeability, a dipole magnet, and a device to alter electron and/or particle trajectory.

Figure 12:
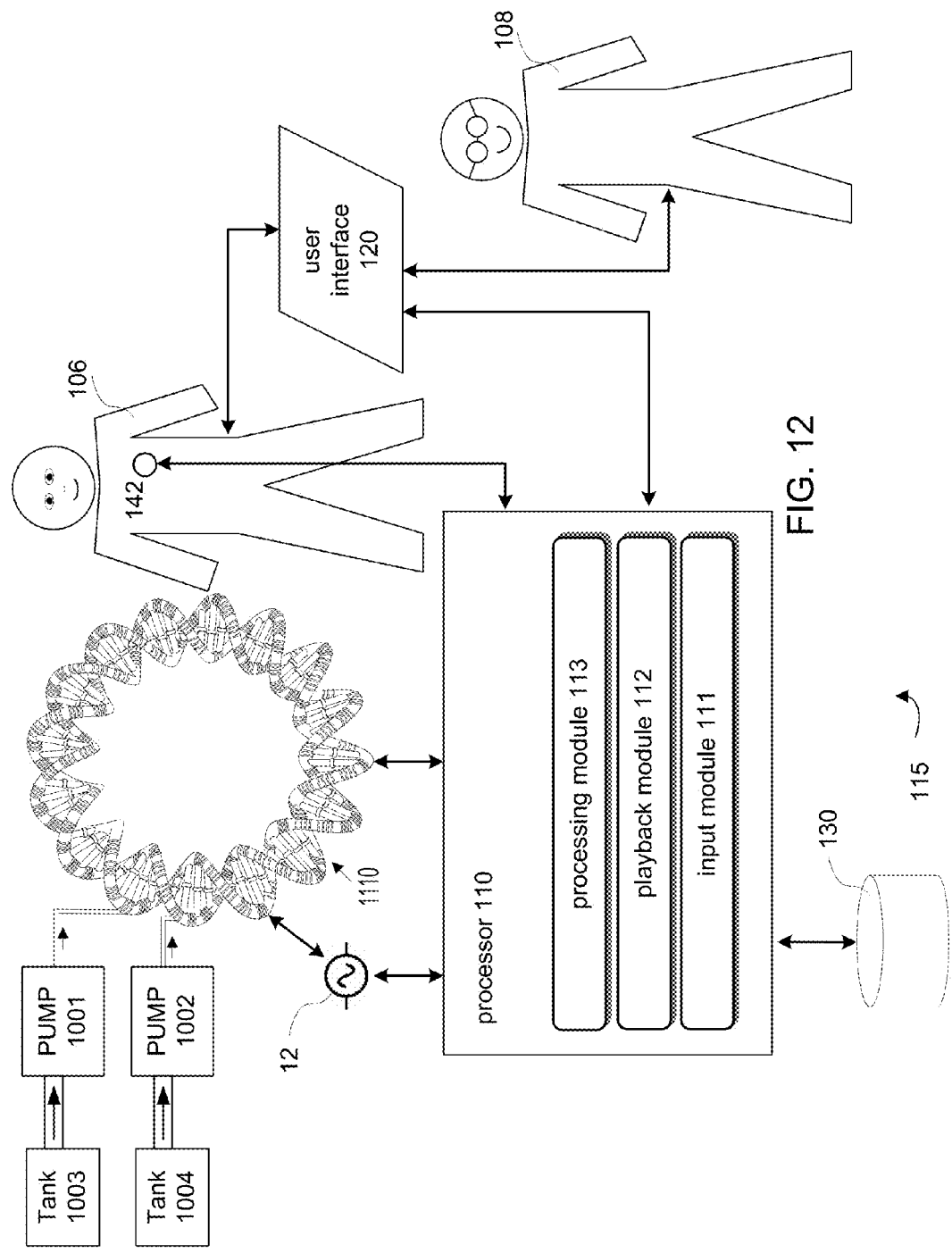
FIG. 12 schematically illustrates a system for providing therapy to a subject, according to one or more embodiments.

By way of illustration, FIG. 12 illustrates an electrical system 115 including a body similar to body 1110 (shown in FIG. 11). Body 1110 may include a first runner and a second runner, which may be similar to or the same as runner 1106 and runner 1108 shown in FIG. 11. Body 1110 may include a first tube and a second tube, which may be similar to or the same as tube 1105 and tube 1107 shown in FIG. 11. Body 1110 may be arranged in a toroidal shape having a first centroid.

Referring to FIG. 12, in some embodiments, body 1110 may be arranged in a toroidal shape. Conductive wires (not shown) may be wound around the runners depicted in FIG. 12. Electrical system 115 may further include one or more of a user interface 120, one or more physical processors 110, one or more sensors 142, electronic storage 130, one or more current sources 12, an input component 111, a playback component 112, a processing component 113, and/or other components.

Sensor(s) 142 may be configured to generate output signals conveying information. The information may include electrophysiological information and/or other information. In some embodiments, the one or more sensors 142 may include one or more of an audio sensor, a microphone, a stethoscope, a pressure sensor, a motion sensor, a proximity sensor, an electromagnetic sensor, an electrode, a temperature sensor, a current sensor, an optical sensor, an electro-optical sensor, and/or other sensors or combinations thereof. In some embodiments, the one or more processors 110 may be configured to provide information-processing capabilities and/or execute computer program components, including but not limited to input component 111, playback component 112, processing component 113, and/or other components. By way of non-limiting example, additional structures and/or features of sensor 142, processor 110, user interface 120, electronic storage 130, input component 111, playback component 112, and/or processing component 113, may be described in U.S. patent application Ser. No. 14/194,412, entitled "Health Applications for Using Bio-Feedback to Control an Electromagnetic Field," which was filed Feb. 28, 2014, which is hereby incorporated into this disclosure by reference in its entirety. This application may also be referred to as "the '412 application" herein.

The one or more current sources 12 may be configured to induce one or more currents across electrical leads, including but not limited to the electrical leads of the one or more conductive wires wound around the runners and/or tubes of body 1110. In some embodiments, the one or more currents may include one or more alternating currents. In some embodiments, one or more induced currents may correspond to one or more sensor-generated output signals. In some embodiments, the one or more induced currents may correspond to one or more signals generated by a transducer and/or one or more other components of system 115.

Referring to FIG. 12, in some embodiments, the current supplied to the conductive wires wound around the runners of body 1110 may be the same or similar with regard to one or more electrical characteristics, including but not limited to frequency, amplitude, power level, and/or other electrical operating characteristics. In some embodiments, one or more electrical characteristics of the currents supplied to the conductive wires wound around the runners of body 1110 may be different.

In some embodiments, an alternating current supplied to body 1110 may include a carrier signal and a modulating signal. In some embodiments, carrier signals used for the alternating current may be radio-frequency signals. As used herein, radio frequency may refer to frequencies between about 30 kHz and about 30 GHz. In some embodiments, the modulating signal for the alternating current may be modulated through one or more of amplitude modulation, frequency modulation, phase modulation, digital modulation, and/or other types of modulation.

In some embodiments, the one or more frequencies included in the alternating current may be based on audio recordings of a note, tone, or chord, generated by a frequency generator and/or a (musical) instrument. For example, a first frequency may be based on the sound of a piano playing an A above middle C (also referred to as A4, which may include sound having a frequency of about 432 Hz, depending on the tuning system used). For example, a second frequency may be based on the sound of some instrument (e.g. a piano) playing a note forming a harmonious interval with A4, e.g. E5, which may include sound having a frequency of about 648 Hz. This tuning may be referred to as Pythagorean tuning. Mathematically perfect tuning may combine notes having a 3:2 ratio. Different types of tuning (or tuning systems), including but not limited to equal tempered tuning, may be used and considered within the scope of this disclosure.

Processor 110 may include one or more of a digital processor, an analog processor, a digital circuit designed to process information, a central processing unit, a graphics processing unit, an analog circuit designed to process information, and/or other mechanisms for electronically processing information. Although processor 110 is shown in FIG. 12 as a single entity, this is for illustrative purposes only. In some embodiments, processor 110 may include a plurality of processing units.

It should be appreciated that although components 111-113 are illustrated in FIG. 12 as being co-located within a single processing unit, in embodiments in which processor 110 includes multiple processing units, one or more of components 111-113 may be located remotely from the other components. The description of the functionality provided by the different components 111-113 described herein is for illustrative purposes, and is not intended to be limiting, as any of components 111-113 may provide more or less functionality than is described. For example, one or more of components 111-113 may be eliminated, and some or all of its functionality may be incorporated, shared, integrated into, and/or otherwise provided by other ones of components 111-113. Note that processor 110 may be configured to execute one or more additional components that may perform some or all of the functionality attributed below to one of components 111-113.

Input component 111 may be configured to obtain information, e.g. from one or more digital audio files, or, alternatively and/or simultaneously, based on sensor-generate output signals. In some embodiments, the information may be obtained from storage, e.g. from electronic storage. Information obtained from storage may include electronic audio files in any format, including but not limited to MP3, WMA, WAV, AIFF, and/or other audio formats. In some embodiments, information may be obtained from sound sources including frequency generators, phonographs, CD-players, DVD players, AM radio, FM radio, and/or other sound sources.

Processing component 113 may be configured to process the obtained information from input component 111. In some embodiments, processing component 113 may be configured to generate a processed signal based on the obtained information from input component 111. For example, processing module 113 may convert, filter, modify, and/or otherwise transform information or signals from input module 111 to generate the processed signal.

Playback component 112 may be configured to produce sound signals based on one or more of the obtained information from input component 111 and/or the processed signal from processing component 113. The sound signals produced by playback component 112 may be coupled electrically to the leads of one or more conductive wires wound around one or more runners of body 85a and/or body 85b such that the induced current corresponds to and/or is based on the sound signals. Alternatively, and/or simultaneously, the induced current may be controlled by and/or based on the sound signals produced by playback component 112. In some embodiments, the sound signals produced by playback module 112 may be amplified by an amplifier before being electrically coupled to the leads of one or more conductive wires. In some preferred embodiments, the amplifier may be an audio amplifier ranging between 100 W and 400 W. Other types of amplifiers and/or amplifiers having a different power range are also contemplated.

Figure 14A:
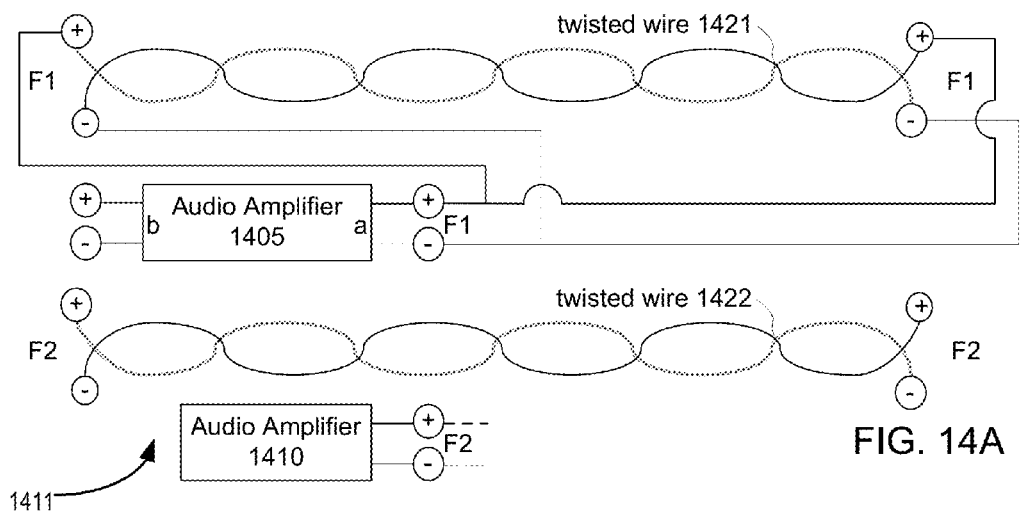
FIGS. 14A and 14B illustrate wiring diagrams for wiring wires around runners, according to one or more embodiments.

FIG. 14A illustrates a wiring diagram 1411 for wiring a twisted wire 1421 and/or a twisted wire 1422 around one or more runners of a body having two or more intertwined helically wound runners, as described elsewhere in this disclosure. In some embodiments, twisted wire 1421 may be wound around a first runner (e.g. the same as or similar to runner 88 shown in FIG. 8). One or more signals may be provided to twisted wire 1421 through four leads (indicated by a circled positive or negative sign in FIG. 14A). The signal provided to twisted wire 1421 may be based on audio recordings of a note, tone, or chord, generated by a frequency generator, a (musical) instrument, and/or another sound source. By way of non-limiting example, the signal may be similar to or based on the information obtained by an input component (e.g. the same as or similar to input component 111 shown in FIG. 12), the processed signal generated by a processing component (e.g. the same as or similar to processing component 113 shown in FIG. 2), a sound signal produced by a playback component (e.g. the same as or similar to playback component 112 shown in FIG. 12), and/or an amplified signal from an audio amplifier 1405. In some embodiments, audio amplifier 1405 may support multiple audio channels, e.g. a channel "a" and a channel "b" as illustrated by labels "a" and "b" in FIG. 14A. The signal on channel "a" of audio amplifier 1405 is labeled "F1." In some embodiments, signal F1 may substantially include and/or be based on a particular frequency. As shown in FIG. 14A, the positive side of signal F1 may be electrically and/or operationally connected to two of the four leads of twisted wire 1421, wherein the two selected leads are on opposite ends of twisted wire 1421. The negative side of signal F1 may be electrically and/or operationally connected to the remaining two of the four leads of twisted wire 1421, which may be on opposite ends of twisted wire 1421.

In some embodiments, wiring diagram 1411 may include a second twisted wire 1422. In some embodiments, twisted wire 1422 may be wound around a second runner (e.g. the same as or similar to runner 89 shown in FIG. 8). One or more signals may be provided to twisted wire 1422 through four leads (indicated by a circled positive or negative sign in FIG. 14A). The signal provided to twisted wire 1422 may, in some embodiments, be the same as the signals provided to twisted wire 1421, e.g. the F1 signal. In some embodiments, the signal provided to twisted wire 1422 may be provided by channel "b" of audio amplifier 1405. In some embodiments, the signal provided to twisted wire 1422 may be provided by one or more channels of an audio amplifier 1410. The signal of audio amplifier 1410 is labeled "F2." In some embodiments, signal F2 may substantially include and/or be based on a particular frequency, which may be a different frequency than the frequency used for signal F1. For example, signal F1 may be based on a frequency of 250 Hz, and signal F2 may be based on a frequency of four times the frequency of signal F1, e.g. 1000 Hz. Likewise, signals F1 and F2 may be 216 Hz and 864 Hz, respectively, by way of non-limiting example. As indicated in FIG. 14A, the positive side of signal F2 may be electrically and/or operationally connected the two positive leads of twisted wire 1422, on opposite ends of twisted wire 1422. The negative side of signal F1 may be electrically and/or operationally connected to the two negative leads of twisted wire 1422, on opposite ends of twisted wire 1422.

Figure 14B:
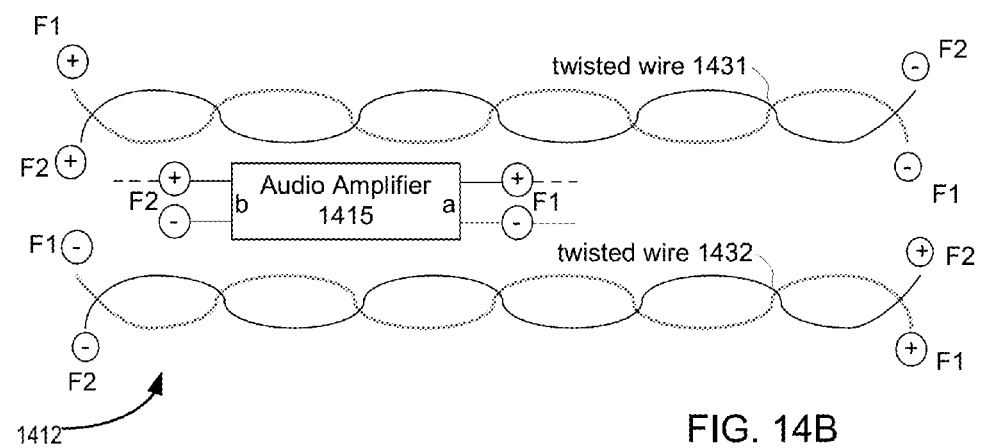

FIG. 14B illustrates a wiring diagram 1412 for wiring a twisted wire 1431 and a twisted wire 1432 around two runners of a body having two intertwined helically wound runners, as described elsewhere in this disclosure. In some embodiments, twisted wire 1431 may be wound around a first runner (e.g. the same as or similar to runner 88 shown in FIG. 8). In some embodiments, twisted wire 1432 may be wound around a second runner (e.g. the same as or similar to runner 89 shown in FIG. 8). One or more signals may be provided to twisted wire 1431 through four leads and to twisted wire 1432 through four leads (indicated by a circled positive or negative sign in FIG. 14B). In some embodiments, the signals provided to twisted wire 1431 and 1432 may be provided by an audio amplifier 1415 that supports multiple audio channels, e.g. a channel "a" and a channel "b" as illustrated by labels "a" and "b" in FIG. 14B. The signal on channel "a" of audio amplifier 1415 is labeled "F1." The signal on channel "b" of audio amplifier 1415 is labeled "F2." As shown in FIG. 14B, the positive side of signal F1 may be electrically and/or operationally connected to two of the eight leads of twisted wires 1431 and 1432, wherein the two selected leads are on opposite ends. The negative side of signal F1 may be electrically and/or operationally connected to two other leads of twisted wires 1431 and 1432, which may be on opposite ends of twisted wire 1421. As shown in FIG. 14B, the positive side of signal F2 may be electrically and/or operationally connected to two of the eight leads of twisted wires 1431 and 1432, wherein the two selected leads are on opposite ends. The negative side of signal F2 may be electrically and/or operationally connected to two other leads of twisted wires 1431 and 1432, which may be on opposite ends of twisted wire 1421. In some embodiments using wiring diagram 1412, signal F1 may be based on a frequency of 250 Hz, and signal F2 may be based on a frequency of four times the frequency of signal F1, e.g. 1000 Hz. Likewise, signals F1 and F2 may be 216 Hz and 864 Hz, respectively, by way of non-limiting example.

In some embodiments, the wiring of two twisted wires around two intertwined helically wound runners as shown in wiring diagram 1411 and/or wiring diagram 1412 may be used as a basis for wiring an electrical system having two, three, or more bodies arranged in each other's proximity. such an electrical system may be the same as or similar to system 1000 shown in FIG. 10 or system 1100 shown in FIG. 11. For example, in an electrical system using two bodies that each include two intertwined helically wound runners, the four runners may be wound with four twisted wires having a total of 16 leads that may be used to electrically and/or operationally connected to 1, 2, and/or 4 audio amplifiers and/or channels thereof that are the same as or similar to audio amplifier 1405, audio amplifier 1410, and/or audio amplifier 1415 (e.g. using channels "a" and "b").

Electronic storage 130 of system 115 in FIG. 12 comprises electronic storage media that electronically stores information. The electronic storage media of electronic storage 130 may include one or both of system storage that is provided integrally (i.e., substantially non-removable) with system 115 and/or removable storage that is connectable to system 115 via, for example, a port (e.g., a USB port, a Firewire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 115 to function properly. For example, electronic storage 130 may store sound information and/or electronic audio files (as discussed elsewhere herein), and/or other information. Electronic storage 130 may be a separate component within system 115, or electronic storage 130 may be provided integrally with one or more other components of system 115 (e.g., processor 110).

User interface 120 of system 115 in FIG. 12 is configured to provide an interface between system 115 and a user (e.g., a user 108, a subject 106, a caregiver, a therapy decision-maker, etc.) through which the user can provide information to and receive information from system 115. This enables data, results, and/or instructions and any other communicable items, collectively referred to as "information," to be communicated between the user and system 115. An example of information that may be conveyed to user 108 is an indication of the volume and/or intensity of the sound signals produced by playback module 112. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 or subject 106 by user interface 120 in the form of auditory signals, visual signals, tactile signals, and/or other sensory signals.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 115 from removable storage (e.g., a smart card, a flash drive, a removable disk, etc.) that enables the user(s) to customize system 115. Other exemplary input devices and techniques adapted for use with system 115 as user interface 120 include, but are not limited to, an RS-232 port, RF link, an IR link, modem (telephone, cable, Ethernet, internet or other). In short, any technique for communicating information with system 115 is contemplated as user interface 120.

Figure 13A:
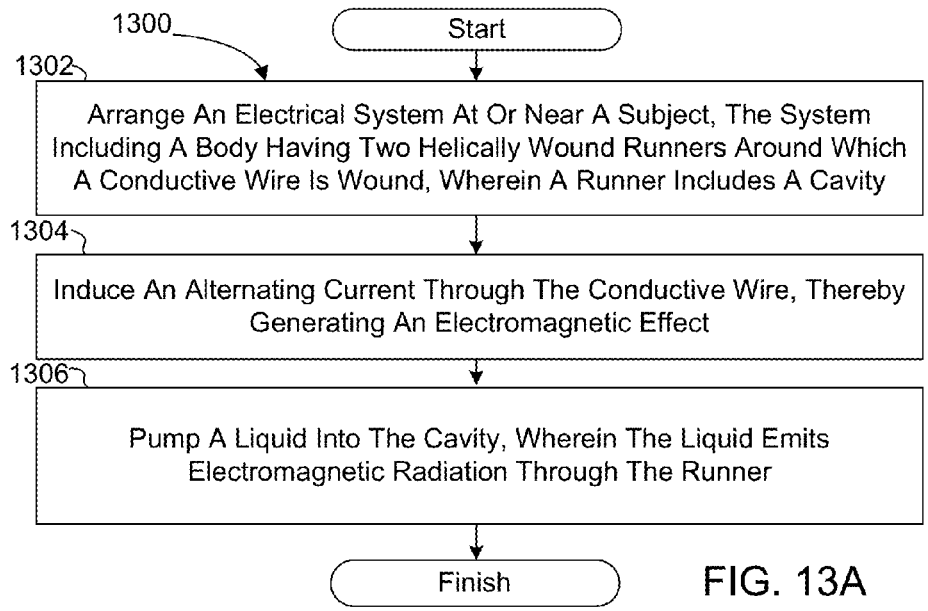
FIGS. 13A and 13B illustrate methods for providing therapy to a subject, according to one or more embodiments.
Figure 13B:
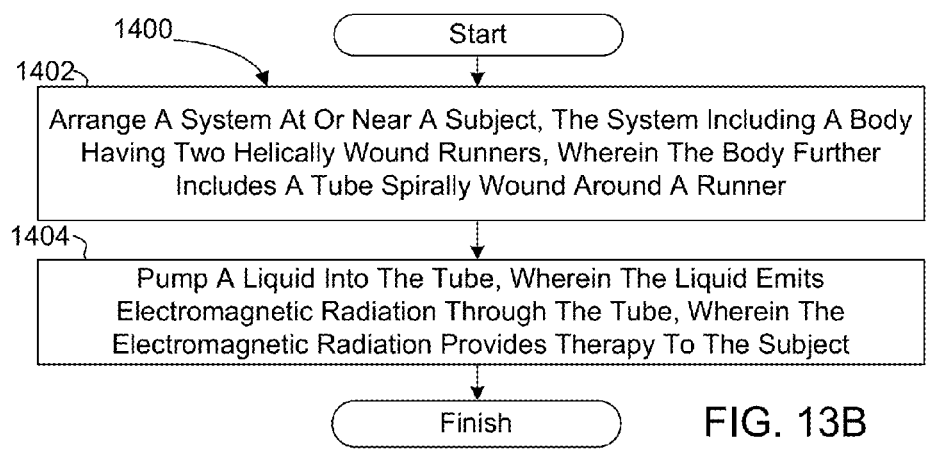

FIGS. 13A and 13B illustrate methods 1300 and 1400 for providing therapy and/or electromagnetic effects to a subject. The operations of methods 1300 and 1400 presented below are intended to be illustrative. In certain embodiments, methods 1300 and 1400 may be accomplished with one or more additional operations not described, and/or without one or more of the operations discussed. Additionally, the order in which the operations of methods 1300 and 1400 are illustrated in FIGS. 13A and 13B and described below is not intended to be limiting.

In certain embodiments, methods 1300 and 1400 may be implemented in one or more processing devices (e.g., a digital processor, an analog processor, a digital circuit designed to process information, an analog circuit designed to process information, and/or other mechanisms for electronically processing information). The one or more processing devices may include one or more devices executing some or all of the operations of methods 1300 and 1400 in response to instructions stored electronically on an electronic storage medium. The one or more processing devices may include one or more devices configured through hardware, firmware, and/or software to be specifically designed for execution of one or more of the operations of methods 1300 and 1400.

Regarding method 1300, at an operation 1302, an electrical system is arranged at or near a subject. The electrical system includes a body. The body includes a first runner and a second runner. The first runner and the second runner are helically intertwined around each other. The body is arranged in a toroidal shape having a centroid. A first conductive wire is wound around the first runner (e.g. as shown in FIG. 8). At least part of the first runner is hollow such that the first runner includes a cavity spanning the first runner longitudinally. The first runner includes material that is non-porous to liquid and that is translucent and/or transparent. In some embodiments, operation 1302 is performed by a system the same as or similar to system 1000 (shown in FIG. 10 and described herein).

At an operation 1304, an alternating current is induced through the first conductive wire such that the alternating current creates an electromagnetic effect at or near the first centroid. The electromagnetic effect may provide therapy to a subject. In some embodiments, operation 1304 is performed by a current source the same as or similar to current source 12 (shown in FIG. 12 and described herein).

At an operation 1306, a liquid is pumped into the cavity of the first runner. The liquid emits electromagnetic radiation through the material of the first runner. The emitted electromagnetic radiation may contribute to the therapy. In some embodiments, operation 1306 is performed by a pump the same as or similar to pump 1001 (shown in FIG. 10 and described herein).

Regarding method 1400, at an operation 1402, a system is arranged at or near the subject. The system includes a body. The body includes a first runner and a second runner. The first runner and the second runner are helically intertwined around each other. The body is arranged in a toroidal shape having a centroid. The body further includes a tube spirally wound around the first runner. The tube includes material that is non-porous to liquid and that is translucent and/or transparent. In some embodiments, operation 1402 is performed by a system the same as or similar to system 1100 (shown in FIG. 11 and described herein).

At an operation 1404, a liquid is pumped into the tube that is wound around the first runner. The liquid emits electromagnetic radiation through the material of the tube. The emitted electromagnetic radiation may provide therapy to the subject. In some embodiments, operation 1404 is performed by a pump the same as or similar to pump 1001 (shown in FIG. 11 and described herein).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. An electrical system comprising:
   a body including:
      a first runner and a second runner that are intertwined and helically wound around each other, wherein at least part of the first runner is hollow such that the first runner includes a cavity spanning the first runner longitudinally, and wherein the first runner includes material that is non-porous to liquid and that is translucent and/or transparent;
      liquid carried in the cavity of the first runner, wherein the liquid emits electromagnetic radiation through the material of the first runner; and
      a first conductive wire spirally wound around the first runner; and
   one or more alternating current sources, wherein the one or more alternating current sources are arranged to electrically couple with the first conductive wire to supply alternating current;
   wherein the electrical system is configured to generate an electromagnetic effect responsive to the alternating current being supplied.

2. The system of claim 1, wherein the system is further configured to provide therapy to a subject in proximity to the system, wherein the provided therapy is provided through the emitted electromagnetic radiation and the generated electromagnetic effect.

3. The system of claim 2, wherein the liquid includes a measurable amount of left-handed molecules, and wherein the second liquid includes a measurable amount of right-handed molecules.

4. The system of claim 3, wherein the left-handed molecules and the right-handed molecules are selected from a set of stereoisomers.

5. The system of claim 3, further comprising one or more pumps configured to pump the liquid along the cavity of the first runner in a first direction and further configured to pump the second liquid along the second cavity of the second runner in a second direction, wherein the first direction is opposite to the second direction.

6. The system of claim 2, wherein the provided therapy includes phototherapy.

7. The system of claim 2, wherein the provided therapy includes photo-bio-modulation.

8. The system of claim 2, wherein the provided therapy interacts with a flow of energy of the subject.

9. The system of claim 1, wherein at least part of the second runner is hollow such that the second runner includes a second cavity spanning the second runner longitudinally, and wherein the second runner includes material that is non-porous to liquid and that is translucent and/or transparent, wherein the body further includes a second liquid carried in the second cavity of the second runner, wherein the second liquid emits, through the material of the second runner, electromagnetic radiation that contributes to the electromagnetic radiation emitted by the liquid carried in the cavity of the first runner, wherein the body further includes a second conductive wire spirally wound around the second runner, wherein the one or more alternating current sources are further arranged to electrically couple with the second conductive wire to supply a second alternating current that contributes to the generated electromagnetic effect.

10. The system of claim 9, further comprising one or more pumps configured to pump the liquid along the cavity of the first runner in a first direction and further configured to pump the second liquid along the second cavity of the second runner in a second direction.

11. The system of claim 10, wherein the first direction is the same as the second direction.

12. The system of claim 10, wherein the first direction is opposite to the second direction.

13. The system of claim 1, further comprising one or more pumps configured to pump the liquid along the cavity of the first runner in a first direction.

14. The system of claim 1, wherein the liquid includes a measurable amount of left-handed molecules.

15. The system of claim 1, wherein the liquid includes a measurable amount of right-handed molecules.

16. The system of claim 1, wherein the electromagnetic effect includes an electromagnetic field.

17. The system of claim 1, wherein the alternating current includes a first carrier signal and a first modulating signal having one or more signal frequencies, and wherein the one or more signal frequencies correspond to one or more spectral characteristics of the emitted electromagnetic radiation through the first runner.

18. The electrical system of claim 1, further comprising:
   one or more physical processors configured via computer-readable instructions to:
      obtain information that includes one or more digital audio files;
      process the obtained information and generate a processed signal based on the obtained information, and
      produce sound signals based on the processed signal, wherein the alternating current is dynamically controlled to correspond to the produced sound signals such that one or more frequencies of the alternating current correspond to one or more frequencies of the produced sound signals.

19. The electrical system of claim 18, wherein the alternating current is dynamically controlled such that one or more frequencies of the emitted electromagnetic radiation correspond to the one or more frequencies of the produced sound signals.

20. A system comprising:
   a body including:
      a first runner and a second runner that are intertwined and helically wound around each other;
      a tube spirally wound around the first runner, wherein the tube includes material that is non-porous to liquid and that is translucent and/or transparent; and
      liquid carried in the tube, wherein the liquid emits electromagnetic radiation through the material of the tube;
   one or more pumps configured to pump the liquid along the tube.

21. The system of claim 20, wherein the system is further configured to provide therapy to a subject in proximity to the system, wherein the provided therapy is provided through the emitted electromagnetic radiation.

22. The system of claim 21, wherein the provided therapy includes phototherapy.

23. The system of claim 21, wherein the provided therapy includes photo-bio-modulation.

24. The system of claim 21, wherein the provided therapy interacts with a flow of energy of the subject.

25. The system of claim 20, wherein the body further includes a second tube that is spirally wound around the second runner, wherein the second tube includes material that is non-porous to liquid and that is translucent and/or transparent, wherein the body further includes a second liquid carried in the second tube, wherein the second liquid emits, through the material of the second tube, electromagnetic radiation that contributes to the electromagnetic radiation emitted by the liquid carried in the tube wound around the first runner, wherein the one or more pumps are further configured to pump the second liquid along the second tube.

26. The system of claim 25, wherein the liquid is pumped in a first direction and the second liquid is pumped in a second direction.

27. The system of claim 26, wherein the first direction is the same as the second direction.

28. The system of claim 26, wherein the first direction is opposite to the second direction.

29. The system of claim 25, wherein the liquid includes a measurable amount of left-handed molecules, and wherein the second liquid includes a measurable amount of right-handed molecules.

30. The system of claim 29, wherein the left-handed molecules and the right-handed molecules are selected from a set of stereoisomers.

31. The system of claim 29, wherein the liquid is pumped in an opposite direction as the second liquid.

32. The system of claim 20, wherein the liquid includes a measurable amount of left-handed molecules.

33. The system of claim 20, wherein the liquid includes a measurable amount of right-handed molecules.

34. The system of claim 20, wherein the body further includes a conductive wire spirally wound around the first runner and one or more alternating current sources, wherein the one or more alternating current sources are configured to electrically couple with the conductive wire to supply alternating current through the conductive wire, wherein the system is configured to generate an electromagnetic effect responsive to the alternating current being supplied, and wherein the electromagnetic effect includes an electromagnetic field.

35. A system comprising:
a body including:
  a first runner and a second runner that are intertwined and helically wound, wherein the first runner is hollow such that the first runner includes a first cavity spanning the first runner longitudinally, wherein the second runner is hollow such that the second runner includes a second cavity spanning the second runner longitudinally, and wherein the first runner and the second runner include material that is non-porous to liquid and that is translucent and/or transparent;
  a first liquid carried in the first cavity of the first runner, wherein the first liquid emits a first type of electromagnetic radiation through the first runner;
  a second liquid carried in the second cavity of the second runner, wherein the second liquid emits a second type of electromagnetic radiation through the second runner;
  a first tube spirally wound around the first runner, wherein the tube includes material that is non-porous to liquid and that is translucent and/or transparent;
  a second tube spirally wound around the second runner, wherein the second tube includes material that is non-porous to liquid and that is translucent and/or transparent;
  a third liquid carried in the first tube, wherein the third liquid emits a third type of electromagnetic radiation through the first tube; and
  a fourth liquid carried in the second tube, wherein the fourth liquid emits a fourth type of electromagnetic radiation through the second tube;
wherein the system is further configured to provide therapy to a subject in proximity to the system, wherein the provided therapy is provided through the first type, the second type, the third type, and the fourth type of emitted electromagnetic radiation.

36. The system of claim 35, further comprising one or more pumps configured to pump one or more of the first liquid, the second liquid, the third liquid, and/or the fourth liquid along the first cavity, the second cavity, the first tube, and/or the second tube, respectively.

37. The system of claim 36, wherein the first liquid is pumped in a first direction, the second liquid is pumped in a second direction, the third liquid is pumped in a third direction, and the fourth liquid is pumped in a fourth direction.

38. The system of claim 37, wherein the first direction and the third direction are opposite to the second direction and the fourth direction.

39. The system of claim 36, wherein the first liquid includes a measurable amount of left-handed molecules.

40. The system of claim 36, wherein the first liquid includes a measurable amount of right-handed molecules.

41. The system of claim 35, wherein the first liquid includes a measurable amount of left-handed molecules.

42. The system of claim 35, wherein the first liquid includes a measurable amount of right-handed molecules.

43. The system of claim 35, wherein the first liquid and the third liquid include a measurable amount of left-handed molecules, and wherein the second liquid and the fourth liquid include a measurable amount of right-handed molecules.

44. The system of claim 43, wherein the left-handed molecules and the right-handed molecules are selected from a set of stereoisomers.

45. The system of claim 35, wherein the provided therapy to the subject includes phototherapy.

46. The system of claim 35, wherein the provided therapy includes photo-bio-modulation.

47. The system of claim 35, wherein the provided therapy interacts with a flow of energy of the subject.

48. A method for providing electromagnetic effects to a subject, the method comprising:
arranging an electrical system at or near the subject, wherein the electrical system includes a body, wherein the body includes a first runner and a second runner, wherein the first runner and the second runner are helically intertwined around each other, wherein the body is arranged in a toroidal shape having a centroid, wherein a first conductive wire is wound around the first runner, wherein at least part of the first runner is hollow such that the first runner includes a cavity spanning the first runner longitudinally, wherein the first runner includes material that is non-porous to liquid and that is translucent and/or transparent;
inducing an alternating current through the first conductive wire such that the alternating current creates an electromagnetic effect at or near the first centroid; and
pumping a liquid into the cavity of the first runner, wherein the liquid emits electromagnetic radiation through the material of the first runner.

49. The method of claim 48, wherein the electromagnetic effect provides therapy to the subject, and wherein the emitted electromagnetic radiation contributes to the provided therapy.

50. The method of claim 49, wherein at least part of the second runner is hollow such that the second runner includes a second cavity spanning the second runner longitudinally, wherein the second runner includes material that is non-porous to liquid and that is translucent and/or transparent, the method further comprising:
pumping a liquid into the cavity of the second runner, wherein the liquid emits electromagnetic radiation through the material of the second runner, wherein the emitted electromagnetic radiation contributes to the provided therapy.

51. The method of claim 50, wherein the liquid in the cavity of the first runner travels in a first direction, wherein the liquid in the cavity of the second runner travels in a second direction.

52. The method of claim 51, wherein the first direction is the same as the second direction.

53. The method of claim 51, wherein the first direction is opposite to the second direction.

54. The method of claim 50, wherein the liquid in the cavity of the first runner includes a measurable amount of left-handed molecules, and wherein the liquid in the cavity of the second runner includes a measurable amount of right-handed molecules.

55. The method of claim 54, wherein the left-handed molecules and the right-handed molecules are selected from a set of stereoisomers.

56. The method of claim 49, wherein the provided therapy includes phototherapy.

57. The method of claim 49, wherein the provided therapy includes photo-bio-modulation.

58. The method of claim 49, wherein the provided therapy interacts with a flow of energy of the subject.

59. The method of claim 58, wherein the provided therapy includes photo-bio-modulation.

60. The method of claim 48, wherein the liquid includes a measurable amount of left-handed molecules.

61. The method of claim 48, wherein the liquid includes a measurable amount of right-handed molecules.

62. The method of claim 48, wherein the electromagnetic effect includes an electromagnetic field.

63. A method for providing therapy to a subject by using electromagnetic effects, the method comprising:
arranging a system at or near the subject, wherein the system includes a body, wherein the body includes a first runner and a second runner, wherein the first runner and the second runner are helically intertwined around each other, wherein the body is arranged in a toroidal shape having a centroid, wherein the body further includes a tube spirally wound around the first runner, wherein the tube includes material that is non-porous to liquid and that is translucent and/or transparent;
pumping a first liquid into the tube wound around the first runner, wherein the first liquid emits electromagnetic radiation through the material of the tube, wherein the emitted electromagnetic radiation provides therapy to the subject.

64. The method of claim 63, wherein the body further includes a second tube spirally wound around the second runner, wherein the second tube includes material that is non-porous to liquid and that is translucent and/or transparent, the method further comprising:
pumping a second liquid into the tube wound around the second runner, wherein the second liquid emits electromagnetic radiation through the material of the second tube, wherein the emitted electromagnetic radiation contributes to the provided therapy.

65. The method of claim 64, wherein the first liquid in the cavity of the first runner travels in a first direction, wherein the second liquid in the cavity of the second runner travels in a second direction.

66. The method of claim 65, wherein the first direction is the same as the second direction.

67. The method of claim 65, wherein the first direction is opposite to the second direction.

68. The method of claim 65, wherein the first liquid in the tube wound around the first runner includes a measurable amount of left-handed molecules, and wherein the second liquid in the second tube wound around the second runner includes a measurable amount of right-handed molecules.

69. The method of claim 68, wherein the left-handed molecules and the right-handed molecules are selected from a set of stereoisomers.

70. The method of claim 63, wherein the first liquid includes a measurable amount of left-handed molecules.

71. The method of claim 63, wherein the first liquid includes a measurable amount of right-handed molecules.

72. The method of claim 63, wherein the provided therapy includes phototherapy.

* * * * *